United States Patent
Armant et al.

(10) Patent No.: US 10,330,680 B2
(45) Date of Patent: Jun. 25, 2019

(54) METHODS OF ASSAYING RNA FROM FETAL EXTRAVILLOUS TROPHOBLAST CELLS ISOLATED FROM A MATERNAL ENDOCERVICAL SAMPLE

(71) Applicant: Wayne State University, Detroit, MI (US)

(72) Inventors: D. Randall Armant, Saint Clair Shores, MI (US); Sascha Drewlo, Grand Rapids, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/517,882

(22) PCT Filed: Oct. 12, 2015

(86) PCT No.: PCT/US2015/055126
§ 371 (c)(1),
(2) Date: Apr. 7, 2017

(87) PCT Pub. No.: WO2016/057993
PCT Pub. Date: Apr. 14, 2016

(65) Prior Publication Data
US 2017/0248599 A1    Aug. 31, 2017

Related U.S. Application Data

(60) Provisional application No. 62/062,433, filed on Oct. 10, 2014.

(51) Int. Cl.
| | | |
|---|---|---|
| C12Q 1/68 | (2018.01) |
| G01N 33/569 | (2006.01) |
| C12Q 1/6804 | (2018.01) |
| C12Q 1/6806 | (2018.01) |
| C12Q 1/6883 | (2018.01) |
| G01N 1/28 | (2006.01) |
| G01N 1/30 | (2006.01) |
| G01N 33/543 | (2006.01) |

(52) U.S. Cl.
CPC ..... *G01N 33/56966* (2013.01); *C12Q 1/6804* (2013.01); *C12Q 1/6806* (2013.01); *C12Q 1/6883* (2013.01); *G01N 1/286* (2013.01); *G01N 1/30* (2013.01); *G01N 33/54326* (2013.01); *G01N 33/56977* (2013.01); *G01N 2001/305* (2013.01)

(58) Field of Classification Search
None
See application file for complete search history.

(56) References Cited

U.S. PATENT DOCUMENTS

| | | |
|---|---|---|
| 5,447,864 A | 9/1995 | Raybuck et al. |
| 5,858,649 A * | 1/1999 | Asgari ............... C12Q 1/6804 435/40.5 |
| 2004/0197832 A1 | 10/2004 | Amiel et al. |
| 2005/0123914 A1 | 6/2005 | Katz et al. |
| 2005/0181429 A1 | 8/2005 | Fejgin et al. |
| 2007/0224597 A1 | 9/2007 | Pircher et al. |
| 2008/0261822 A1 | 10/2008 | Fejgin et al. |
| 2009/0286271 A1 | 11/2009 | Karumanchi et al. |
| 2011/0183338 A1 | 7/2011 | Bischoff |
| 2012/0149014 A1 | 6/2012 | Allman et al. |
| 2013/0171672 A1 | 7/2013 | Hussa et al. |
| 2015/0267240 A1 | 9/2015 | Armant et al. |

FOREIGN PATENT DOCUMENTS

WO    WO-2014/062995 A1    4/2014

OTHER PUBLICATIONS

Bajpayee, S., Prenatal Genetic Diagnosis Using Transcervically Derived and Immunomagnetically Isolated Trophoblast Cells, Wayne State University Honors College Theses, Dec. 13, 2012.
Bolnick, J. et al., Trophoblast retrieval and isolation from the cervix (TRIC) for noninvasive prenatal screening at 5 to 20 weeks of gestation, *Fertility and Sterility*, 102(1): 135-142, Jul. 2014.
Bolnick, A. et al., Trophoblast Retrieval and Isolation from the Cervix for Noninvasive, First Trimester, Fetal Gender Determination in a Carrier of Congenital Adrenal Hyperplasia, *Reproductive Sciences*, pp. 1-6, Feb. 25, 2016.
Fritz, R. et al., Noninvasive detection of trophoblast protein signatures linked to early pregnancy loss using trophoblast retrieval and isolation from the cervix (TRIC), *Fertility and Sterility*, 104(2): 339, Aug. 2015.
Fritz, R. et al., Trophoblast retrieval and isolation from the cervix (TRIC) is unaffected by early gestational age or maternal obesity, *Prenatal Diagnosis*, 35: 1218-22, 2015.
Huang, Y. et al., Acquisition of fetal cells from transcervical cells in early pregnancy and immunocytochemical study, Dept. of Obstetrics and Gynecology, Nanfang Hospital, Southern Medical University, Guangahou, China (Abstract).
Imudia, A. et al., Transcervical Retrieval of Fetal Cells in the Practice of Modern Medicine: A Review of the Current Literature and Future Direction, *Fertil Steril*, 93(6): 1725-30, Apr. 2010.
Imudia, A. et al., Retrieval of trophoblast cells from the cervical canal for prediction of abnormal pregnancy: a pilot study, *Human Reproduction*, 24(9): 2086-92, Jun. 4, 2009.

(Continued)

Primary Examiner — Carla J Myers
(74) Attorney, Agent, or Firm — Dinsmore & Shohl LLP

(57) ABSTRACT

Methods of isolating and assaying fetal extravillous trophoblast cells, including assays of RNA of the fetal extravillous trophoblast cells according to aspects of the disclosure include obtaining a maternal endocervical sample containing fetal extravillous trophoblast cells from a pregnant subject; fixing the maternal endocervical sample in an aldehyde fixative, removing fetal extravillous trophoblast cells from the maternal endocervical sample thereby producing isolated extravillous trophoblast cells, isolating and assaying RNA from the fetal extravillous trophoblast cells.

13 Claims, 11 Drawing Sheets

(56) References Cited

OTHER PUBLICATIONS

Katz-Jaffe, M. et al., DNA identification of fetal cells isolated from cervical mucus: potential for early non-invasive prenatal diagnosis, *BJOG: An International Journal of Obstetrics and Gynecology*, 112: 595-600, May 2005.

Evers, D. et al., The effect of formaldehyde fixation on RNA: optimization of formaldehyde adduct removal, The Journal of Molecular Diagnostics, 13(3): 282-288, May 1, 2001.

* cited by examiner

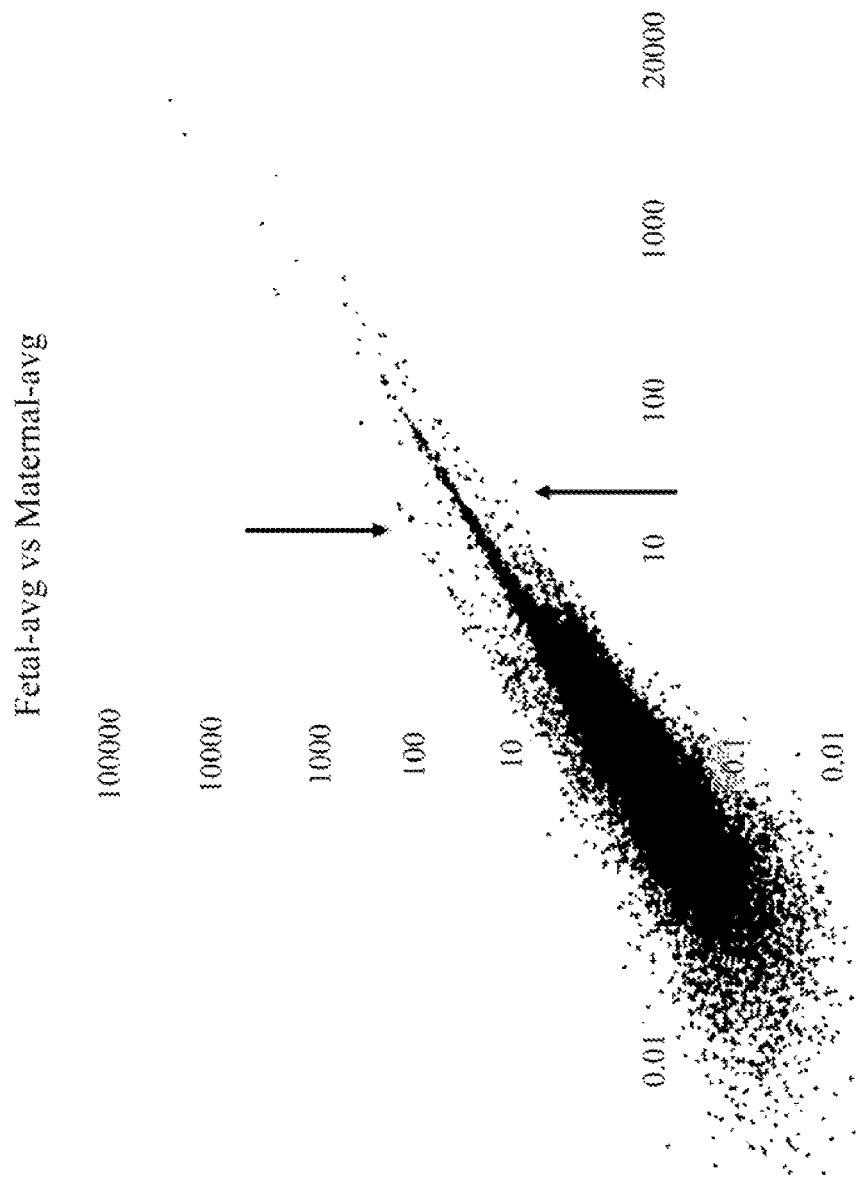

US 10,330,680 B2

METHODS OF ASSAYING RNA FROM FETAL EXTRAVILLOUS TROPHOBLAST CELLS ISOLATED FROM A MATERNAL ENDOCERVICAL SAMPLE

REFERENCE TO RELATED APPLICATION

This application claims priority from U.S. Provisional Patent Application Ser. No. 62/062,433, filed Oct. 10, 2014, the entire content of which is incorporated herein by reference.

FIELD OF THE INVENTION

The present disclosure relates generally to isolated fetal extravillous trophoblast cells and methods of assay of prenatal detection and diagnosis of genetic variations and pathological conditions. According to specific aspects of the disclosure, methods of isolating and assaying RNA of fetal extravillous trophoblast cells and mass spectroscopy methods of assay of protein of the fetal extravillous trophoblast cells from a fetus of an ongoing pregnancy are described herein.

BACKGROUND OF THE INVENTION

Prenatal detection and diagnosis of genetic variations and pathological conditions are useful for monitoring and maintenance of health and well-being of both mother and fetus. Non-invasive methods are lacking for obtaining and analyzing fetal cells which are typically few in number. There is a continuing need for assays to alert clinicians to abnormalities in ongoing pregnancies, such as Down Syndrome and other chromosome number disorders, diagnosis of inherited diseases, and pathologies of the fetus in pregnancies in which preeclampsia or intrauterine growth restriction will develop.

SUMMARY OF THE INVENTION

Methods of assaying RNA from fetal extravillous trophoblast cells according to aspects of the present invention include: obtaining a maternal endocervical sample from a pregnant subject; removing fetal extravillous trophoblast cells from the maternal endocervical sample; fixing fetal extravillous trophoblast cells by treatment with an aldehyde fixative producing aldehyde fixed fetal extravillous trophoblast cells; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample, producing isolated fetal extravillous trophoblast cells; fixing isolated fetal extravillous trophoblast cells by treatment with an aldehyde fixative producing aldehyde fixed isolated fetal extravillous trophoblast cells; lysing the aldehyde fixed isolated fetal extravillous trophoblast cells, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the treatment with the aldehyde fixative is performed prior to and/or following removing the fetal extravillous trophoblast cells from the maternal endocervical sample; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample, producing isolated fetal extravillous trophoblast cells; fixing fetal extravillous trophoblast cells by treatment with an aldehyde fixative producing aldehyde fixed fetal extravillous trophoblast cells, wherein the treatment with the aldehyde fixative is performed prior to and/or following removing fetal extravillous trophoblast cells from the maternal endocervical sample; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample, producing isolated fetal extravillous trophoblast cells; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells and wherein the treatment with the aldehyde fixative is performed prior to and/or following isolating fetal extravillous trophoblast cells from the maternal endocervical sample; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells and wherein the treatment with the aldehyde fixative is performed prior to and/or following isolating fetal extravillous trophoblast cells from the maternal endocervical sample; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject; removing fetal extravillous trophoblast cells from the maternal endocervical sample producing isolated fetal extravillous trophoblast cells; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject, fixing the cells in the maternal endocervical sample in an aldehyde fixative immediately after obtaining the sample from the pregnant subject; removing fetal extravillous trophoblast cells from the maternal endocervical sample; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant subject, fixing the cells in the maternal endocervical sample in an aldehyde fixative immediately after obtaining the sample from the pregnant subject; removing fetal extravillous trophoblast cells from the maternal endocervical sample; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the treatment with the aldehyde fixative is performed prior to and/or following isolating fetal extravillous trophoblast cells from the maternal endocervical sample; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the treatment with the aldehyde fixative is performed prior to and/or following isolating fetal extravillous trophoblast cells from the maternal endocervical sample; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells and wherein the treatment with the aldehyde fixative is performed prior to and/or following isolating fetal extravillous trophoblast cells from the maternal endocervical sample; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells and wherein the treatment with the aldehyde fixative is performed prior to and/or following isolating fetal extravillous trophoblast cells from the maternal endocervical sample; washing the aldehyde fixed fetal extravillous trophoblast cells to promote removal of the crosslinks introduced by the aldehyde fixative, producing lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject; removing fetal extravillous trophoblast cells from the maternal endocervical sample; fixing fetal extravillous trophoblast cells by treatment with an aldehyde fixative producing aldehyde fixed fetal extravillous trophoblast cells, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject, fixing the cells in the maternal endocervical sample in an aldehyde fixative immediately after obtaining the sample from the pregnant subject; removing fetal extravillous trophoblast cells from the maternal endocervical sample; washing the aldehyde fixed fetal extravillous trophoblast cells to promote removal of the crosslinks introduced by the aldehyde fixative, producing washed fetal extravillous trophoblast cells; extracting fetal extravillous trophoblast cell RNA from the washed fetal extravillous trophoblast cells; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include: obtaining a maternal endocervical sample from a pregnant human subject, fixing the cells in the maternal endocervical sample in an aldehyde fixative immediately after obtaining the sample from the pregnant subject; removing fetal extravillous trophoblast cells from the maternal endocervical sample; lysing the isolated fetal extravillous trophoblast cells following aldehyde fixation, producing a lysate, washing the lysate to promote removal of the crosslinks introduced by the aldehyde fixative, producing washed lysate; extracting fetal extravillous trophoblast cell RNA from the washed lysate; and assaying the fetal extravillous trophoblast cell RNA to determine one or more characteristics of the fetal extravillous trophoblast cell RNA.

Methods of assaying RNA from fetal extravillous trophoblast cells according to aspects of the present invention include assaying the fetal extravillous trophoblast cell RNA by sequencing, PCR, quantitative PCR, real-time PCR or a combination of any two or more thereof.

Methods of assaying RNA from fetal extravillous trophoblast cells according to aspects of the present invention include removing fetal extravillous trophoblast cells from the maternal endocervical sample comprises contacting the fetal extravillous trophoblast cells with an antibody specific for the fetal extravillous trophoblast cells, wherein the antibody does not bind to maternal cells in the maternal endocervical sample.

Methods of assaying RNA from fetal extravillous trophoblast cells according to aspects of the present invention include removing fetal extravillous trophoblast cells from the maternal endocervical sample comprises contacting the fetal extravillous trophoblast cells with an antibody specific for the fetal extravillous trophoblast cells, wherein the antibody does not bind to maternal cells in the maternal endocervical sample and wherein the antibody specific for the fetal extravillous trophoblast cells is attached to a support.

Methods of assaying RNA from fetal extravillous trophoblast cells according to aspects of the present invention are described in which no Protein A or Protein G is attached to the support.

Methods of assaying RNA from fetal extravillous trophoblast cells according to aspects of the present invention include removing fetal extravillous trophoblast cells from the maternal endocervical sample comprises contacting the fetal extravillous trophoblast cells with an antibody specific for the fetal extravillous trophoblast cells, wherein the antibody does not bind to maternal cells in the maternal endocervical sample and wherein the antibody specific for the fetal extravillous trophoblast cells is attached to a support, wherein the support is a plurality of magnetic particles and removing fetal extravillous trophoblast cells from the maternal endocervical sample comprises exposure of the magnetic particles to a magnet.

Methods of assaying RNA from fetal extravillous trophoblast cells according to aspects of the present invention are described in which the maternal endocervical sample is not treated with a mucolytic agent.

Methods of assaying fetal extravillous trophoblast cells according to aspects of the present invention include obtaining a maternal endocervical sample from a pregnant subject; contacting the maternal endocervical sample with a first antibody, the first antibody specific for the fetal extravillous trophoblast cells, wherein the first antibody does not bind to maternal cells in the maternal endocervical sample; contacting the maternal endocervical sample with one more additional antibodies, wherein the first antibody and each additional antibody is distinguishably labeled with different labels detectable by inductively coupled plasma mass spectrometry; nebulizing the maternal endocervical sample to separate cells; and performing inductively coupled plasma mass spectrometry on the cells, thereby assaying the fetal extravillous trophoblast cells.

Methods of assaying fetal extravillous trophoblast cells according to aspects of the present invention include obtaining a maternal endocervical sample from a pregnant subject; contacting the maternal endocervical sample with a first antibody, the first antibody specific for the fetal extravillous trophoblast cells, wherein the first antibody is specific for major histocompatibility complex, class I, G (HLA-G); contacting the maternal endocervical sample with one more additional antibodies, wherein the first antibody and each additional antibody is distinguishably labeled with different labels detectable by inductively coupled plasma mass spectrometry; nebulizing the maternal endocervical sample to separate cells; and performing inductively coupled plasma mass spectrometry on the cells, thereby assaying the fetal extravillous trophoblast cells.

Methods of assaying fetal extravillous trophoblast cells according to aspects of the present invention include obtaining a maternal endocervical sample from a pregnant subject; contacting the maternal endocervical sample with a first antibody, the first antibody specific for the fetal extravillous trophoblast cells, wherein the first antibody does not bind to maternal cells in the maternal endocervical sample; contacting the maternal endocervical sample with one more additional antibodies, wherein the one or more additional antibodies is an antibody specific for a protein selected from the group consisting of: galectin 13, galectin 14, placental growth factor, pregnancy-associated plasma protein A, alpha fetal protein, endoglin, fms-related tyrosine kinase 1 and keratin-7, wherein the first antibody and each additional antibody is distinguishably labeled with different labels detectable by inductively coupled plasma mass spectrometry; nebulizing the maternal endocervical sample to separate cells; and performing inductively coupled plasma mass spectrometry on the cells, thereby assaying the fetal extravillous trophoblast cells.

Methods of assaying fetal extravillous trophoblast cells according to aspects of the present invention include obtaining a maternal endocervical sample from a pregnant subject; contacting the maternal endocervical sample with a first antibody, the first antibody specific for the fetal extravillous trophoblast cells, wherein the first antibody is specific for major histocompatibility complex, class I, G (HLA-G); contacting the maternal endocervical sample with one more additional antibodies, wherein the one or more additional antibodies is an antibody specific for a protein selected from the group consisting of: galectin 13, galectin 14, placental growth factor, pregnancy-associated plasma protein A, alpha fetal protein, endoglin, fms-related tyrosine kinase 1 and keratin-7, wherein the first antibody and each additional antibody is distinguishably labeled with different labels detectable by inductively coupled plasma mass spectrometry; nebulizing the maternal endocervical sample to separate cells; and performing inductively coupled plasma mass spectrometry on the cells, thereby assaying the fetal extravillous trophoblast cells.

Methods of assaying fetal extravillous trophoblast cells and/or RNA from fetal extravillous trophoblast cells according to aspects of the present invention are described wherein the maternal endocervical sample is not treated with a mucolytic agent.

According to aspects of the present invention, a sample is collected at about three weeks after conception in an ongoing pregnancy (gestational age 5 weeks) up to about 20 weeks of gestation (mid-point of pregnancy) or later.

BRIEF DESCRIPTION OF THE DRAWINGS

FIG. 4C is a plot showing results of RNA sequencing and comparison of RNA expression levels in fetal and maternal samples as RPKM values and demonstrating differences between fetal and maternal samples;

DETAILED DESCRIPTION OF THE INVENTION

Figure 1:
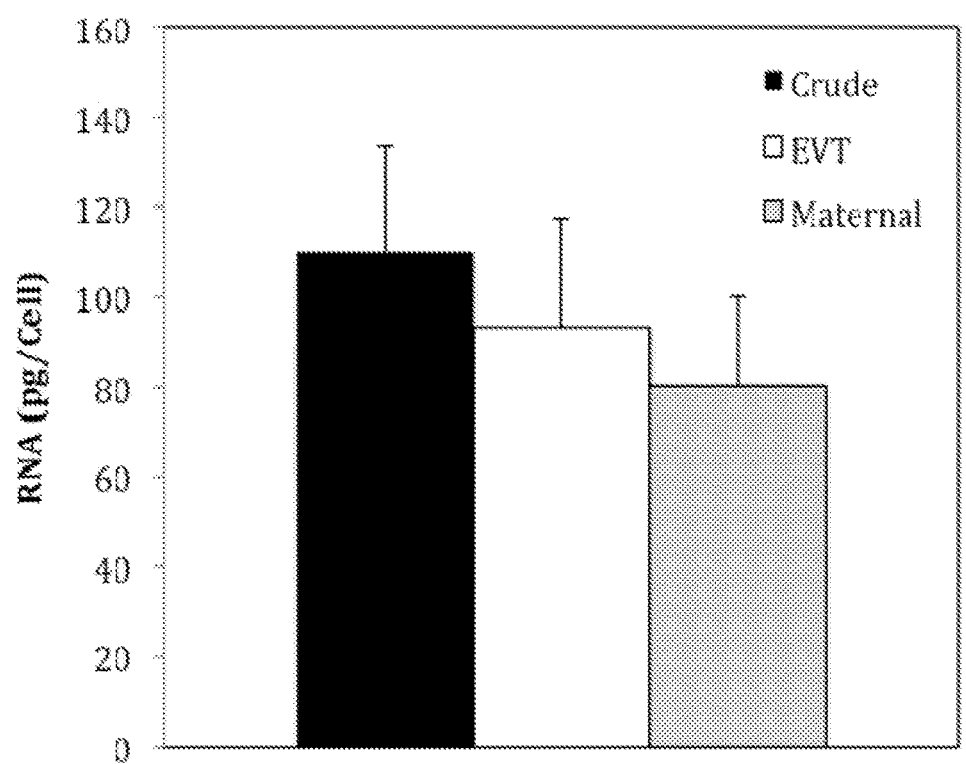
FIG. 1 is a graph showing RNA recoveries from 19 maternal endocervical specimens, the RNA isolated from "crude" ThinPrep specimens, isolated fetal extravillous trophoblast cells (EVT) or fetal extravillous trophoblast cell-depleted samples containing maternal cells.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

Compositions and methods relating to isolation and assay of fetal cells from a fetus of an ongoing pregnancy are provided according to aspects of the present invention.

Analysis of fetal cells provides information about the fetus, such as gender, and allows for detection of fetal abnormalities, including chromosomal aneuploidies, as well as pregnancy-associated disorders including preeclampsia, intrauterine growth restriction, spontaneous abortion and preterm birth.

Analysis of fetal cells allows for detection of biomarkers of pregnancy-associated disorders including preeclampsia, intrauterine growth restriction, spontaneous abortion and preterm birth.

Assays described herein are optionally assays of one or more biomarkers expressed by fetal extravillous trophoblast cells to detect changes indicative of abnormal placental function such as preeclampsia, intrauterine growth restriction, spontaneous abortion and preterm birth.

While compositions and methods described herein with particular reference to human females and human fetuses, they are not limited to humans and fetal cells of other species may be similarly isolated and analyzed.

Methods of Isolating Fetal Extravillous Trophoblast Cells

Methods of isolating fetal extravillous trophoblast cells are provided according to aspects of the present invention which include obtaining a maternal endocervical sample containing fetal extravillous trophoblast cells from a pregnant subject; treating the fetal extravillous trophoblast cells with a nuclease; and removing fetal extravillous trophoblast cells from the maternal endocervical sample, thereby isolating the fetal extravillous trophoblast cells.

A maternal endocervical sample is collected from a pregnant female from about 1 week to about 45 weeks of pregnancy, such as in the first trimester, second trimester and/or third trimester of pregnancy.

According to aspects of the present invention, a sample is collected from a pregnant subject at about three weeks after conception (gestational age 5 weeks) up to about 20 weeks of gestation (mid-point of pregnancy) or later.

Treating the fetal extravillous trophoblast cells with a nuclease is accomplished using any nuclease effective to cleave DNA and/or RNA. Such nucleases include endonucleases and exonucleases. Non-limiting examples of nucleases that can be used to treat fetal extravillous trophoblast cells include deoxyribonucleases (DNAses), including but not limited to: DNAse I, DNAse II, lambda exonuclease, nuclease Bal-31, exoribonucleases, *E. coli* exonucleases I II, III, IV, V, VI, VII, and VIII, restriction endonucleases such as Aat II, Acc I, Acu I, Afl III, Age I, Ale I, Alu I, Alw I, Alw44 I, Apa I, Apo I, Asc I, Ase I, Asn I, Ava I, Ava II, Bae I, BamH I, Ban I, Ban II, Bcl I, Bgl I, Bgl II, Bln I, Blp I, Bmr I, Bmt I, Bpm I, Bsg I, Bsm I, Bsr I, BssH II, BstE II, Btg I, Bts I, Cfo I, Cla I, Dde I, Dpn I, Dpn II, Dra I, Drd I, Eae I, Eag I, Ear I, Eci I, EclX I, EcoR I, EcoR II, EcoR V, Fat I, Fau I, Fok I, Fse I, Hae II, Hae II, Hga I, Hha I, Hinc II, Hind III, Hpa I, Hpa II, Kas I, Kpn I, Ksp I, Mbo I, Mbo II, Mfe I, Mlu I, MluN I, Mly I, Mme I, Mnl I, Msc I, Mse I, Msp I, Mwo I, Nae I, Nar I, Nci I, Nco I, Nde I, Nde II, Nhe I, Not I, Nru I, Nsi I, Nsp I, Pac I, Pci I, Ple I, Pme I, Pml I, Psi I, Psp I, Pst I, Pvu I, Pvu II, Rsa I, Sac I, Sal I, Sap I, Sbf I, Sau3A I, Sca I, ScrF I, Sfcl, Sfi I, Sfol, Sma I, Sml I, Spe I, Sph 1, Ssp I, Stu I, Sty I, Swa I, Taq I, Xba I, Xho I Xma I and Xmn I, *E. coli* endonuclease I or II, T7 endonuclease, T4 endonuclease, micrococcal nuclease, RecBCD endonuclease, SI nuclease, P1 nuclease and mung bean nuclease. Non-limiting examples of nucleases that can be used to treat fetal extravillous trophoblast cells include ribonucleases (RNAses), including endoribonucleases and exoribonucleases such as RNase A, RNase D, RNase H, RNase L, RNase P, RNase PH, RNase PhyM, RNase R, RNase T1, RNase T2, RNase U2, Polynucleotide Phosphorylase, oligoribonuclease, exoribonuclease I, Exoribonuclease II, RNase I, RNase II and RNase III.

Optionally, fetal extravillous trophoblast cells are treated with two or more nucleases.

Nuclease treatment of fetal extravillous trophoblast cells is performed under nuclease reaction conditions, typically in a physiological buffer at physiological pH and temperature.

Nuclease treatment of fetal extravillous trophoblast cells is performed without fixation of the cells, prior to fixation or following fixation of the cells according to aspects of methods of the present invention.

Nuclease treatment of fetal extravillous trophoblast cells is performed prior to isolation of the fetal extravillous trophoblast cells from the maternal endocervical sample or following isolation of the fetal extravillous trophoblast cells from the maternal endocervical sample according to aspects of methods of the present invention. It is appreciated that nuclease treatment of fetal extravillous trophoblast cells performed prior to isolation of the fetal extravillous trophoblast cells from the maternal endocervical sample is also treatment of the maternal endocervical sample with a nuclease.

Nuclease treatment of a maternal endocervical sample is performed without fixation of the sample, prior to fixation or following fixation of the sample according to aspects of methods of the present invention.

Optionally, a one or more nucleases is attached to a support and the fetal extravillous trophoblast cells are treated with the one or more nucleases by contacting the fetal extravillous trophoblast cells and the one or more nucleases attached to the support under nuclease reaction conditions. The support is sized to prevent entry into fetal extravillous trophoblast cells and/or maternal cells of a maternal endocervical sample. In a preferred option, the fetal extravillous trophoblast cells treated with one or more nucleases attached to a support are fixed fetal extravillous trophoblast cells.

A support be solid or semi-solid and is insoluble in aqueous solutions. The support can be any of various materials such as glass, silicon, silica gel, clay, paper, a synthetic or naturally occurring polymer, such as polyethylene, polyesters, polyamides, polyurethanes, polyepoxides, polystyrene, polycarbonate, polypropylene, polyvinylchloride, polyvinylacetate, PVDF, polymethacrylates, nylon, cellulose, cellulose esters, mixed cellulose esters, cellulose ethers, cross-linked alginic acid, substituted and cross-linked guar gums, agar, agarose, gelatins, dextran, and polyacrylamides, mixtures, copolymers and terpolymers of such polymers or any other material to which a nuclease can be attached.

A support used can include functional groups for binding a nuclease, such as, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of a nuclease to a support is achieved by any of various methods, illustratively including adsorption and chemical bonding. In one example, 1-Ethyl-3-[3-dimethylaminopropyl] carbodiimide hydrochloride, EDC or EDAC chemistry, can be used to attach a nuclease to a support. A nuclease can be bonded directly or indirectly to the material of the support, for example, via bonding to a coating or linker disposed on the support. Functional groups, modification thereof and attachment of a protein to a support are known in the art, for example as described in Fitch, R. M., Polymer Colloids: A Comprehensive Introduction, Academic Press, 1997.

A support for attachment of a nuclease can be in any of a variety of forms and shapes including, but not limited to, microtiter plates, microtiter wells, pins, fibers, beads, slides, silicon chips and membranes such as a nitrocellulose or PVDF membrane.

Optionally, a nuclease is attached to a support which is in the form of a particle. Such particles can be solid or semi-solid particles of any of a variety of shapes and sizes. Particles are illustratively organic or inorganic particles, such as glass or metal and can be particles of a synthetic or naturally occurring polymer, such as polystyrene, polycarbonate, silicon, nylon, cellulose, agarose, dextran, polyacrylamide; and latex beads.

The support and attached nuclease has a size which prohibits entry into fixed cells, for example, a particle size greater than 10 nm in diameter.

According to aspects of the present invention, removing fetal extravillous trophoblast cells from the maternal endocervical sample is accomplished by contacting the fetal extravillous trophoblast cells with an antibody specific for the fetal extravillous trophoblast cells, wherein the antibody does not bind to maternal cells in the maternal endocervical sample, and capturing the fetal extravillous trophoblast cells attached to the antibodies.

According to particular aspects of methods of the present invention, the antibody is specific for major histocompatibility complex, class I, G (HLA-G).

Optionally, the antibody specific for the fetal extravillous trophoblast cells is attached to any solid or semi-solid which is insoluble in aqueous solutions, such as those described herein for attachment of a nuclease. Attachment of the antibody to the support is achieved by any of various methods, illustratively including adsorption and chemical bonding as described herein for attachment of a nuclease.

Optionally, the antibody specific for the fetal extravillous trophoblast cells is directly attached to a support. The term "directly attached" is used to indicate that the support is covalently or non-covalently bound to the antibody specific for the fetal extravillous trophoblast cells and that the support is not bound to the antibody via a secondary antibody.

In a further option, the antibody specific for the fetal extravillous trophoblast cells is attached to a support without an intervening Protein A or Protein G molecule. Thus, according to particular aspects of methods of the present invention, no Protein A or Protein G is attached to the support.

The Antibody Specific for the Fetal Extravillous Trophoblast Cells is Attached to any Insoluble Support According to particular aspects of methods of the present invention, the support is a plurality of magnetic particles and removing fetal extravillous trophoblast cells from the maternal endocervical sample includes exposure of the magnetic particles to a magnet.

Magnetic nanoparticles directly coupled to the antibody which specifically binds to a fetal antigen typically have a size in the range of 10 nm-1 um, although smaller or larger magnetic nanoparticles may be used.

According to particular aspects of methods of the present invention, HLA-G antibody is attached to magnetic nanoparticles.

Optionally, methods of isolating fetal extravillous trophoblast cells further include fixing cells of the maternal endocervical sample by treatment with a fixative, wherein the treatment with the fixative is performed prior to or following isolating fetal extravillous trophoblast cells from the maternal endocervical sample.

Treating the fetal extravillous trophoblast cells with a nuclease is optionally performed prior to or following removing fetal extravillous trophoblast cells from the maternal endocervical sample.

The fixative used can be glutaraldehyde; formaldehyde; paraformaldehyde; or a combination of any two or more thereof. According to particular aspects of methods of the present invention, the aldehyde fixative is paraformaldehyde.

Optionally, the maternal endocervical sample is first fixed in a non-aldehyde fixative. The fetal extravillous trophoblast cells are then fixed with an aldehyde fixative. The non-aldehyde fixative is optionally removed or partly removed by washing the maternal endocervical sample with a physiological liquid or buffer, such as saline or a buffer compatible with mammalian cells.

Non-aldehyde fixatives illustratively include acetone, acetic acid, and alcohols such as ethanol and methanol. Combinations of two or more non-aldehyde fixatives are optionally used. According to aspects of the present invention, a mixture of methanol and acetic acid is used as a non-aldehyde fixative.

According to particular aspects of methods of the present invention, the fetal extravillous trophoblast cells are further treated with a protease and/or a glycosaminoglycan degrading enzyme (GAGase), wherein treating the fetal extravillous trophoblast cells with a protease and/or a GAGase is performed prior to or following removing fetal extravillous trophoblast cells from the maternal endocervical sample and prior to or following treatment of the fetal extravillous trophoblast cells with a nuclease.

Glycosaminoglycan degrading enzymes include, for example, hyaluronidase, heparinase and chondroitinase.

According to particular aspects of methods of the present invention, the maternal endocervical sample is not treated with a mucolytic agent. According to particular aspects of methods of the present invention, the maternal endocervical sample is not treated with a mucolytic agent selected from N-acetyl-L-cysteine, DTT, trypsin and trypsin/EDTA. According to particular aspects of methods of the present invention, the maternal endocervical sample is not treated with one or more of a collagenase, a protease, a liberase blendzyme, and a mucolytic agent.

Optionally, a maternal endocervical sample is acidified prior to isolating fetal extravillous trophoblast cells. An acidifying agent is optionally added to the sample bringing the pH of the sample to about pH 5-6. An acidifying agent can be any acid or acidic buffer, for example.

Methods according to aspects of the present invention optionally further include assay of the isolated fetal extravillous trophoblast cells. According to aspects of the present invention, fetal extravillous trophoblast cells are isolated and analyzed to aid in diagnosis and treatment of the fetus and/or woman pregnant with the fetus to promote the health of the fetus and/or woman pregnant with the fetus.

Such assays include an assay of one or more proteins or peptides of fetal extravillous trophoblast cells and/or an assay of one or more nucleic acids of fetal extravillous trophoblast cells.

Binding assays are optionally used in assays fetal extravillous trophoblast cells according to aspects of the present invention.

A binding assay is an assay in which a target analyte, such as a biomarker, is detected by binding with a binding partner. The term "binding partner" refers to a biological molecule capable of specific binding to a target analyte. Non-limiting examples of binding partners include antibodies, aptamers, receptors, ligands and substrates for enzymatic action of a target analyte. Binding partners may also be nucleic acid probes. The skilled artisan can routinely identify, isolate and/or make binding partners and use them in binding assays. Such techniques are well-known to those of ordinary skill in the art.

A binding assay can be performed according to any of various methods that allow for detection of one or more target analytes by binding to a binding partner. Binding of a target analyte and binding agent can be detected directly or indirectly, such as by use of detectable labels.

Nucleic acid assays such as sequencing, an amplification assay and/or a hybridization assay can be used to detect expression of a target analyte of isolated fetal extravillous trophoblast cells, such as a biomarker. DNA is isolated from fetal extravillous trophoblast cells according to standard DNA extraction procedures. RNA is preferably isolated from fetal extravillous trophoblast cells as described herein according to aspects of the present invention.

Nucleic acid assays, include, but are not limited to, amplification reactions such as polymerase chain reactions (PCR), such as RT-PCR; dot blot; in situ hybridization; Northern blot; and RNase protection. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

A nucleic acid probe or primer able to hybridize to a target analyte mRNA or cDNA to detect and/or quantify mRNA or cDNA can be used in a nucleic assay. A nucleic acid probe can be an oligonucleotide of at least 10, 15, 30, 50 or 100 nucleotides in length and sufficient to specifically hybridize under stringent conditions to a target mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof. The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

A sample from a non-human animal is optionally purified for assay according to a method of the present invention.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "amplification assay" refers to a method for copying a template nucleic acid, thereby producing nucleic acids which include copies of all or a portion of the template nucleic acid.

Amplification assays include those which include template directed primer extension catalyzed by a nucleic acid polymerase using a pair of primers which flank the target nucleic acid, illustratively including, but not limited to, polymerase chain reaction (PCR), reverse-transcription PCR (RT-PCR), ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004. The term "primer" refers to a single stranded oligonucleotide, typically about 9-60 nucleotides in length, that may be longer or shorter, and that serves as a point of initiation for template-directed DNA synthesis.

Appropriate reactions conditions for in vitro nucleic acid amplification methods include presence of suitable reaction components including, but not limited to, a polymerase and nucleotide triphosphates. One of skill in the art will be able to determine conditions suitable for amplification of the target nucleic acids with only routine experimentation using primers of the present invention including choice of factors such as buffer, nucleotides, pH, Mg salt concentration, primer concentration and temperature. The nucleic acid product of the amplification methods optionally contains additional materials such as, but not limited to, non-target nucleic acid sequences, functional groups for chemical reaction and detectable labels, present in the primers and not present in the original DNA template. PCR may also being performed as quantitative PCR (Q-PCR) also known as real-time PCR or kinetic PCR (KPCR). Q-PCR is used to amplify and simultaneously quantify a targeted DNA molecule.

The terms "quantitative PCR" or "Q-PCR" refer to a variety of methods for quantifying the results of polymerase chain reactions. Q-PCR methods generally determine or compare the amplification factor, such as determining the threshold cycle (Ct), or are co-amplification methods that compare the amount of produce generated from simultaneous amplification of target and standard templates. Many Q-PCR techniques include reporter probes, intercalator dyes or both. Reporter probes include, but are not limited to, TaqMan® probes (Applied Biosystems), molecular beacons, Scorpion® primers, Lux™ primers and FRET primers; and intercalator dyes include, but are not limited to, ethidium bromide, SYBR® Green I (Molecular Probes) and PicoGreen® (Molecular Probes).

For one or more specific sequences in a DNA sample, Real Time-PCR enables both detection and quantification. The quantity can be either an absolute number of copies or a relative amount when normalized to DNA input or additional normalizing genes. Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target. For example TaqMan probes are used. The TaqMan probe principle relies on the 5'-3' exonuclease activity of Taq polymerase to cleave a dual-labeled probe during hybridization to the complementary target sequence and fluorophore-based detection. As in other real-time PCR methods, the resulting fluorescence signal permits quantitative measurements of the accumulation of the product during the exponential stages of the PCR; however, the TaqMan probe significantly increases the specificity of the detection. TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescin, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer) As long as the fluorophore and the quencher are in proximity, quenching inhibits any fluorescence signals.

TaqMan probes are designed such that they anneal within a DNA region amplified by a specific set of primers. As the Taq polymerase extends the primer and synthesizes the nascent strand (again, on a single-strand template, but in the direction opposite to that shown in the diagram, i.e. from 3' to 5' of the complementary strand), the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

PCR is employed for whole genome amplification according to aspects of the present invention.

Hybridization assays for a nucleic acid target include, but are not limited to, dot blot, nucleic acid hybridization, bead assays, in situ hybridization, Northern blot, Southern blot and microarray assays. Details of such assays are described in J.

Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

Nucleic acid hybridization assays include use of a nucleic acid probe which specifically hybridizes to a target nucleic acid under defined hybridization and wash conditions. The term "probe" encompasses nucleic acid sequences of various lengths, typically at least about 9 to about 8000 nucleotides in length, but may be shorter or longer as long as the probe is capable of specifically hybridizing to a target nucleic acid in a nucleic acid hybridization assay. A probe may be single or double stranded and may be generated by recombinant methods, chemical synthesis, isolation from natural sources, or a combination of two or more of these.

Sequencing methodologies useful in various assays, such as to compare transcriptomes and identify biomarkers, include massively parallel signature sequencing, single-molecule real-time sequencing, polony sequencing, ion semiconductor (Ion Torrent sequencing), pyrosequencing (454), sequencing by synthesis (Illumina), sequencing by ligation (SOLiD sequencing), chain termination (Sanger sequencing), for example.

Fetal RNA is isolated from fetal extravillous trophoblast cells for assay according to aspects of the present invention.

Methods of isolating and/or assaying RNA from fetal extravillous trophoblast cells are provided according to aspects of the present invention which include obtaining a maternal endocervical sample from a pregnant subject; treating the fetal extravillous trophoblast cells with a DNAse; removing fetal extravillous trophoblast cells from the maternal endocervical sample; fixing fetal extravillous trophoblast cells by treatment with an aldehyde fixative producing aldehyde fixed fetal extravillous trophoblast cells; washing the aldehyde fixed fetal extravillous trophoblast cells to promote removal of the crosslinks introduced by the aldehyde fixative, producing washed fetal extravillous trophoblast cells; and extracting fetal extravillous trophoblast cell RNA from the washed fetal extravillous trophoblast cells.

Methods of isolating and/or assaying RNA from fetal extravillous trophoblast cells are provided according to aspects of the present invention wherein the fetal extravillous trophoblast cells are not treated with a DNAse prior to lysis of the fetal extravillous trophoblast cells, which include obtaining a maternal endocervical sample from a pregnant subject; removing fetal extravillous trophoblast cells from the maternal endocervical sample; fixing fetal extravillous trophoblast cells by treatment with an aldehyde fixative producing aldehyde fixed fetal extravillous trophoblast cells; washing the aldehyde fixed fetal extravillous trophoblast cells to promote removal of the crosslinks introduced by the aldehyde fixative, producing washed fetal extravillous trophoblast cells; and extracting fetal extravillous trophoblast cell RNA from the washed fetal extravillous trophoblast cells. Extracting fetal extravillous trophoblast cell RNA from the washed fetal extravillous trophoblast cells includes lysis of the washed fetal extravillous trophoblast cells, producing lysed fetal extravillous trophoblast cells.

The lysed fetal extravillous trophoblast cells are treated with DNase and a protease to degrade fetal extravillous trophoblast cell DNA and proteins.

The fetal extravillous trophoblast cell RNA is assayed to determine one or more characteristics of the fetal extravillous trophoblast cell RNA and is optionally compared to a standard.

The treatment of the fetal extravillous trophoblast cells with the aldehyde fixative is optionally performed prior to and/or following isolating fetal extravillous trophoblast cells from the maternal endocervical sample.

In a further option, the maternal endocervical sample is fixed immediately after obtaining the sample from the pregnant subject. The maternal endocervical sample is further optionally fixed in a non-aldehyde fixative immediately after obtaining the sample from the pregnant subject and prior to fixing fetal extravillous trophoblast cells by treatment with the aldehyde fixative producing aldehyde fixed fetal extravillous trophoblast cells. In still a further option, the maternal endocervical sample is fixed by treatment with the aldehyde fixative immediately after obtaining the sample from the pregnant subject.

The fetal extravillous trophoblast cells are optionally treated with a DNAse before or after isolation from the maternal endocervical sample.

According to preferred aspects, intact fetal extravillous trophoblast cells are not treated with a DNAse before or after isolation from the maternal endocervical sample. Lysed fetal extravillous trophoblast cells are treated with a DNAse to remove fetal extravillous trophoblast cell DNA in a process of isolating fetal extravillous trophoblast cell RNA.

Cells can be fixed with an aldehyde fixative selected from glutaraldehyde, formaldehyde, paraformaldehyde and mixtures of any two or more thereof. According to aspects, cells are fixed with paraformaldehyde.

Fixation of fetal extravillous trophoblast cells is performed under aldehyde fixation conditions. Aldehyde fixation conditions include aldehyde fixative concentration, optional buffer, time and temperature.

The concentration of the aldehyde fixative used depends on the desired fixation time and temperature to be used. The concentration of the aldehyde fixative used is typically in a range from 0.1 to 10 percent w/v of the aqueous solution, such as 0.5 to 6 percent w/v by weight of the aqueous solution or 1 to 4 percent w/v of the aqueous solution.

Aldehyde fixative may be prepared dissolution of the fixative in an aqueous solution. The aqueous solution is optionally buffered, such as by a physiological buffer at physiological pH.

Fixation temperature can be varied, for example, depending on the fixation time desired. Fixation temperature is typically in the range of about 4° C.-40° C.

Crosslinks introduced by the aldehyde fixation are at least partially removed by treatment of the aldehyde fixed fetal extravillous trophoblast cells by washing in an aqueous wash solution under defined conditions of heat and salt. Removal of crosslinks introduced by the aldehyde fixation can be achieved by washing cells in a wash solution in a physiological buffer at physiological pH in the range of about pH 7.0-8.0, exemplified by, but not limited to, a phosphate buffer such as PBS, a Tris buffer such as Tris-HCl, HEPES or triethanolamine buffer, at a temperature in the range of 4° C.-80° C. for a time in the range of several days (for temperatures lower than room temperature)—15 minutes (for temperatures over about 60° C.). Removal of crosslinks introduced by the aldehyde fixation can be achieved, example, by washing of cells in a solution with higher than physiological salt concentrations, such as a NaCl concentration in the range of 160 mM-300 mM for a time in the range of several days—15 minutes. Combinations of heat and higher than physiological salt concentrations can be used.

A stabilizing agent is optionally included in the wash solution, exemplified by, but not limited to, EDTA. EDTA is optionally present in amounts in the range of 0.1 mM-20 mM, 0.5 mM-10 mM or 0.75-5 mM.

Particular conditions for at least partial removal of crosslinks introduced by aldehyde fixation and assessment of removal of the aldehyde crosslinks are described in Darling et al., Anal. Chem., 86:5678-5681, 2014; and Niranjanakumari S. et al., Methods 2002; 26: 182-190.

Lysis of the cells is accomplished by any of various methods, illustratively including sonication or treatment with detergent.

Isolated fetal extravillous trophoblast cells are washed prior to lysis to at least partially remove crosslinks introduced by aldehyde fixation according to aspects of the present invention.

The washed fetal extravillous trophoblast cells are further processed to isolate RNA. Such processing includes lysis of the fetal extravillous trophoblast cells and separation of fetal extravillous trophoblast cell DNA and protein from the RNA. Separation of fetal extravillous trophoblast cell DNA and protein from the RNA is accomplished by any of various methods, illustratively including, degradation of the fetal extravillous trophoblast cell DNA by DNAse treatment of the lysed cells and/or degradation of the protein by protease treatment of the lysed cells. Optionally, a protease is included in the wash solution.

The RNA can then be further purified to remove the DNAse and/or protease and degraded DNA and/or proteins, by any of various methods, exemplified by precipitation and washing.

Alternatively, the isolated fetal extravillous trophoblast cells are lysed and the fetal extravillous trophoblast cell lysate lysate is washed to at least partially remove crosslinks introduced by aldehyde fixation according to aspects of the present invention, producing a washed fetal extravillous trophoblast cell lysate.

Lysis of the isolated fetal extravillous trophoblast cells and washing to at least partially remove crosslinks introduced by aldehyde fixation is performed simultaneously according to aspects of the present invention by inclusion of a detergent in the wash solution. A detergent is optionally included in the wash solution, for example in amounts in the range of 0.1-5% w/v of the wash solution, 0.25-2.5% w/v or 0.5-1.5% w/v. Included detergents are exemplified by, but not limited to, SDS, Nonidet P-40, Tween-20 and Triton-X 100. An example wash solution for simultaneous lysis is 200 mM NaCl, 10 mM Tris-HCl pH 8.0, 1 mM EDTA and 1% SDS. A further example wash solution for simultaneous lysis is 200 mM NaCl, 10 mM Tris-HCl pH 8.0, 1 mM EDTA, 1% SDS and a protease, such as Proteinase K in the range of 50-1500 micrograms/ml.

The washed fetal extravillous trophoblast cell lysate is further processed to isolate RNA. Such processing includes separation of fetal extravillous trophoblast cell DNA and protein from the RNA. Separation of fetal extravillous trophoblast cell DNA and protein from the RNA is accomplished by any of various methods, illustratively including, typically by degradation of the fetal extravillous trophoblast cell DNA by DNAse treatment of the lysed cells and/or protease treatment of the lysed cells. DNAse is typically used in amounts in the range of about 50-500 Kunitiz Units/milliliter of lysate. The RNA can then be further purified to remove the DNAse and degraded DNA and/or proteins, by any of various methods, exemplified by precipitation, centrifugation and washing.

Assaying the fetal extravillous trophoblast cell RNA includes any applicable nucleic acid assay.

The isolated RNA is optionally used to construct libraries for "next-generation sequencing" by generating barcoded libraries using the ScriptSeq v2 RNA-Seq Library Preparation Kit (Epicentre).

RNA isolated from fetal and maternal cells can be sequenced to identify gene products in fetal and maternal cells. Comparison of the gene products in different cell populations is used to identify commonalities and differences indicative of health as well as pathologies or the fetus and/or mother associated with pregnancy such as preeclampsia, intrauterine growth restriction, preterm labor and miscarriage.

The RNA can be reverse transcribed to cDNA for analysis using qPCR. The invented process can be used to identify genes that are differentially expressed by fetal extravillous trophoblast cells between 5 and 20 weeks of gestation in pregnancies with normal outcomes, compared to pregnancies with adverse outcomes (preeclampsia, intrauterine growth restriction, preterm labor, miscarriage and others) according to aspects of the present invention. Once identified, isolated RNA can be used for nucleic acid assays, such as quantitative RT-PCR, to prospectively screen patients to assess their risk for an adverse outcome, for example.

Immunoassay methods can be used to assay a target analyte such as a biomarker in a sample, including, but not limited to, enzyme-linked immunosorbent assay (ELISA), enzyme-linked immunofiltration assay (ELIFA), flow cytometry, immunoblot, immunoprecipation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005. and J. Sambrook and D. W. Russell, Molecular Cloning: A Laboratory Manual, Cold Spring Harbor Laboratory Press, 3rd Ed., 2001.

Antibodies and methods for preparation of antibodies are well-known in the art. As used herein, the terms "antibody" and "antibodies" encompass monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the terms "antibody fragment" and "antigen-binding fragment" defines a fragment of an antibody that immunospecifically binds to a target analyte. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). Antibody fragments are also produced by recombinant DNA technologies.

Antibodies, antigen-binding fragments, methods for their generation and methods for screening of generated antibodies for substantially specific binding to an antigen are known in the art and such antibodies, antigen binding fragments and methods are described in further detail, for instance, in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975). Antibodies for target analytes, such as a biomarker, can be produced in animals, synthesized, produced by recombinant methods and/or obtained commercially.

Aptamers can be used to assay a target analyte. The term "aptamer" refers to a peptide and/or nucleic acid that substantially specifically binds to a specified substance. In the case of a nucleic acid aptamer, the aptamer is characterized by binding interaction with a target other than Watson/Crick, base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Detecting binding between a target analyte present in a sample and a binding partner is achieved by any of various methods known in the art, illustratively including detection of a detectable label directly or indirectly attached to the target analyte or the binding partner. The term "detectable label" refers to a material capable of producing a signal indicative of the presence of the detectable label by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, an electron dense particle, a magnetic particle, an enzyme, a substrate, a radioisotope and a chromophore.

The identity of a particular detectable label or labels used depends on the detection process used. Such detection processes are incorporated in particular assay formats illustratively including ELISA, Western blot, immunoprecipitation, immunocytochemistry, immuno-fluorescence assay, liquid chromatography, flow cytometry, other detection processes known in the art, or combinations thereof.

A binding assay can incorporate a binding partner attached to a support. A support with attached binding partner used in a binding assay can be solid or semi-solid and can be any of various materials such as glass, silicon, paper, a synthetic or naturally occurring polymer, such as polystyrene, polycarbonate, polypropylene, PVDF, nylon, cellulose, agarose, dextran, and polyacrylamide or any other material to which a binding partner can be stably attached for use in a binding assay.

A support used can include functional groups for binding to binding partners, such as, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of binding partners to a support is achieved by any of various methods, illustratively including adsorption and chemical bonding. In one example, 1-Ethyl-3-[3-dimethylaminopropyl]carbodiimide hydrochloride, EDC or EDAC chemistry, can be used to attach binding partners to particles. The binding partners can be bonded directly or indirectly to the material of the support, for example, via bonding to a coating or linker disposed on the support. Functional groups, modification thereof and attachment of a binding partner to a support are known in the art, for example as described in Fitch, R. M., Polymer Colloids: A Comprehensive Introduction, Academic Press, 1997.

Such supports can be in any of a variety of forms and shapes including, but not limited to, microtiter plates, microtiter wells, pins, fibers, beads, slides, silicon chips and membranes such as a nitrocellulose or PVDF membrane.

Any of various spectroscopy methods can be used to assay a target analyte, such as a biomarker, according to embodiments of the present invention, including, but not limited to, gas chromatography, liquid chromatography, ion mobility spectrometry, mass spectrometry, liquid chromatography-mass spectrometry (LC-MS or HPLC-MS), ion mobility spectrometry-mass spectrometry, tandem mass spectrometry, gas chromatography-mass spectrometry, matrix-assisted desorption ionization time-of-flight (MALDI-TOF) mass spectrometry, surface-enhanced laser desorption ionization (SELDI) and nuclear magnetic resonance spectroscopy, all of which are well-known to the skill artisan.

Optionally, spectrometric analysis is used to assay a sample for a target analyte such as a biomarker. Mass analysis can be used in an assay according to aspects of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Mass spectrometry using isolated cells.

Biomarkers for adverse pregnancy outcomes have previously been limited to those that can be detected in maternal circulation, which are generally proteins secreted by the placenta or other affected organs. Proteins released by the placenta need to reach a certain threshold (in 2nd and 3rd trimester) for detection in the maternal blood.

Mass spectrometry (MS) analysis of isolated fetal extravillous trophoblast cells according to aspects of methods of the present invention provides sensitive analysis of a small number of cells. A typical maternal endocervical sample yields 500-2000 fetal EVT cells. MS methods according to aspects of methods of the present invention allow analysis of a small number of cells.

High Resolution Phenotyping Using Mass Spectrometry

Methods of assaying fetal extravillous trophoblast cells are provided according to aspects of the present invention which include obtaining a maternal endocervical sample from a pregnant subject; contacting the maternal endocervical sample with a first antibody, the first antibody specific for the fetal extravillous trophoblast cells, wherein the first antibody does not bind to maternal cells in the maternal endocervical sample; contacting the maternal endocervical sample with one more additional antibodies, wherein the first antibody and each additional antibody is distinguishably labeled with different labels detectable by inductively coupled plasma mass spectrometry; nebulizing the maternal endocervical sample to separate cells; and performing inductively coupled plasma mass spectrometry on the cells, thereby assaying the fetal extravillous trophoblast cells.

Targeted mass spectrometry is used for sensitive and quantitative detection of proteins, peptides and post-translational modifications according to aspects of the present invention. To increase sensitivity and to quantify specific proteins peptides can be introduced into the mass spectometry biomarkers which can be used to quantify proteins on small sample sizes.

"CytoTof" is optionally used for deep phenotyping of fetal extravillous trophoblast cell-specific proteins according to aspects of the present invention. "CytoTof" combines mass spectrometry and antibody labeling of proteins on cells. Antibodies against specific targets are labeled with different isotopes which makes them distinguishable by mass spectrometry process. Cells to be assayed are labeled with the antibodies, nebulised, and time of flight is measured for each mass/metal labeled antibody and quantified. This approach makes it possible to analyse up to 100 markers on one single cell. In this method the fetal extravillous trophoblast cells are not required to be purified. HLA-G positivity can be used as an identifier in the deep phenotyping process and the high single cell resolution.

Standards

Standards suitable for assays are well-known in the art and the standard used can be any appropriate standard.

In one example, a standard is a result of an assay of a biomarker in a comparable sample from a control animal.

A standard may be a reference level of the one or more biomarkers previously determined in a sample of an individual control animal or in a population of control animals and stored in a print or electronic medium for recall and comparison to a result of an assay of the one or more biomarkers in an animal to which a test compound is administered.

A standard can be a result of an assay of the one or more biomarkers in a comparable sample from an animal at a different time. For example, a standard can be a result of an assay of the one or more biomarkers in a comparable sample obtained from the same animal at a different time, prior to or after administration of the test compound. A first sample can be obtained from an individual animal at a first time to obtain an animal-specific baseline level of the one or more biomarkers in the first sample. A second sample can be obtained from the individual animal at a second time and assayed for the one or more biomarkers to monitor differences in the levels of the one or more biomarkers compared to the first sample. Additional samples can be obtained from the animal at additional time points and assayed for the one or more indicators to monitor differences in the levels of the one or more indicators compared to the first sample, second sample or other samples.

A standard can be an average level of one or more biomarkers in comparable samples obtained from one or more populations. The "average level" is determined by assay of the one or more indicators in comparable samples obtained from each animal of the population. The term "comparable sample" is used to indicate that the samples are of the same type, i.e. each of the comparable samples is a serum sample, for example.

A difference detected in levels or expression of one or more biomarkers in assays of the present invention compared to a standard can be an increase or decrease in level or expression of the one or more biomarkers. The magnitude of the increase or decrease can be, for example, at least 5%, 10%, 15%, 20%, 25%, 30%, 35%, 40%, 45%, 50%, 55%, 60%, 65%, 70%, 75%, 80%, 85%, 90%, 95%, 99%, or more, of the standard level.

Assay results can be analyzed using statistical analysis by any of various methods, exemplified by parametric or nonparametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone (publisher); 5th Ed., 2009; and Freund, R J et al., Statistical Methods, Academic Press; 3rd Ed., 2010.

Assays described herein are optionally assays of one or more biomarkers expressed by fetal extravillous trophoblast cells. For example, one or more of galectin 13 (LGALSI3, a.k.a. PP13), galectin 14 (LGALSI4), placental growth factor (PGF), pregnancy-associated plasma protein A (PAPPA), alpha fetal protein (AFP), endoglin (ENG), or fms-related tyrosine kinase 1 (FLT-1) is assayed to detect changes indicative of abnormal placental function such as preeclampsia, intrauterine growth restriction, spontaneous abortion and preterm birth.

Assays described herein are optionally assays of one or more biomarkers expressed by fetal extravillous trophoblast cells of a fetus of first and second trimester pregnancies such as one or more of galectin 13 (LGALS13, a.k.a. PP13), galectin 14 (LGALS14), placental growth factor (PGF), pregnancy-associated plasma protein A (PAPPA), alpha fetal protein (AFP), endoglin (ENG), or fms-related tyrosine kinase 1 (FLT-1).

Embodiments of inventive compositions and methods are illustrated in the following examples. These examples are provided for illustrative purposes and are not considered limitations on the scope of inventive compositions and methods.

EXAMPLES

Example 1

Isolation of Non-Fixed Fetal Extravillous Trophoblast Cells and Isolation of DNA from Unfixed Fetal Extravillous Trophoblast Cells A maternal endocervical sample is collected using a cytobrush and the cytobrush is rinsed in ice-cold culture medium or PBS (137 mM NaCl, 10 mM Phosphate buffer).

Cells are centrifuged and resuspended in 10 ml PBS plus 2.7 mM $CaCl_2$, 1 mM $MgCl_2$ warmed to room temperature.

DNase I is prepared by dissolving 1 mg DNase I powder (Worthington Cat #2138, >2000 Kunitz units/mg) in 10 ml PBS plus 0.9 mM MgCl2.

A 100 µl aliquot of the DNase solution is added to the cells and incubated for 15 mins at room temperature. The cells are then washed three times with 10 ml PBS containing 30 mM EDTA and then a further two washes with PBS are performed.

The cells are centrifuged through a 250 micron filter and resuspended in 10 ml PBS at 4° C. The cells are then washed 2 more times in 10 ml PBS and the final pellet is brought to a volume of 1 ml in PBS.

The magnetic separation procedure for removing fetal cells is started by addition of 20 ul of 250 nm magnetic nanoparticles conjugated to an anti-HLA-G antibody are added to the washed cells after resuspension in 1 ml PBS and incubated at 4° C. for 1 to 24 hours with shaking.

Maternal cells (HLA-G negative) are separated from magnetized (HLA-G positive) fetal extravillous trophoblast cells using a DynaMag™ Spin magnet (Life Technologies).

The fetal extravillous trophoblast cells are then washed 3 times using magnet to remove residual maternal cells.

The isolated fetal extravillous trophoblast cells are resuspended in a solution of 50-100 microliters PBS/10 mM EDTA. Optionally, the isolated maternal cells are resuspended in a solution of 50-100 microliters PBS/10 mM EDTA. An aliquot of 15 microliters is removed for cell counting and quality control for fetal cells and optionally maternal cells if desired.

Aliquots of 50 microliters each of isolated maternal cells and isolated fetal extravillous trophoblast cells are used for DNA isolation.

Aliquots of 25 microliters of 3× concentrated DNA extraction buffer (90 mM TRIS, 90 mM EDTA, 1.5% EDTA, pH 8.0, 3 mg/ml Proteinase K) are added to 50 microliters of the isolated maternal cells or isolated fetal extravillous trophoblast cells for DNA isolation. These mixtures are then incubated for 3 hrs at 65° C., followed by 10 min at 95° C. The extracted DNA is frozen for PCR assays or can be for further purified by centrifugation at high speed in a microcentrifuge for 5 minutes. Optionally the DNA is still further purified, for example using commercial DNA purification and concentration kits, such as a Zymresearch DNA 10 concentration kit. Pico green of similar reagents can be used for DNA quantification.

Non-fixed cells were incubated with or without DNase either on beads or in solution. Fresh cells treated with soluble DNase resulted on average in production of 3-6 ng total DNA.

DNA purification of low amounts of DNA with the Zymresearch DNA concentrator kit led to a 30-50% loss of DNA. On average 2-4 ng pure high-quality DNA is isolated from a single sample of maternal endocervical material retrieved with a cytobrush.

Example 2

Isolation of Fixed Fetal Extravillous Trophoblast Cells and Isolation of DNA from Fixed Fetal Extravillous Trophoblast Cells A maternal endocervical sample is collected using a cytobrush by inserting it approximately 2 cm into the endocervical canal and rotating 2 or 3 times as it is withdrawn. Mucus present in the canal is also collected in the brush. The cytobrush is rinsed in fixative, for example, using a ThinPrep kit. The specimen is stored refrigerated or at ambient temperature and transported to the laboratory for further processing. It can be stored at 4° C. for at least one week without loss of RNA or HLA-G protein.

To isolate fetal extravillous trophoblast cells and optionally maternal cells, all cells are washed twice with PBS after acidification of the maternal endocervical sample by adding 0.6 ml of acetic acid to the 20-ml volume of ThinPrep containing the cells, achieving a final concentration of 3% acetic acid.

The cells are centrifuged through a 250 micron filter and resuspended in 10 ml PBS at 4° C. The cells are then washed 2 more times in 10 ml PBS and the final pellet is brought to a volume of 1 ml in PBS.

To protect nuclear DNA from degradation by nucleases entering the fixed, permeable cell, the DNAse is attached, such as by covalent linkage, to one or more supports such as beads or particles that cannot penetrate the fixed cells. In this example, DNAse covalently bound to non-magnetic beads is added to the cells, 5 microliters of F7 (MoBiotec, Germany), and incubated for 10 mins at room temperature.

The magnetic separation procedure for removing fetal cells is started for 1 hr to 24 hrs with shaking, as described in Bolnick et al., Fertil. Steril., 102:135-142.e6, 2014.

Maternal cells (HLA-G negative) are separated from magnetized (HLA-G positive) fetal extravillous trophoblast cells using a DynaMag™ Spin magnet (Life Technologies).

The fetal extravillous trophoblast cells are then washed 3 times in PBS with 30 mM of EDTA.

Optionally, the maternal cells are purified using 15 micron mesh, the cells are then washed and concentrated.

The isolated fetal extravillous trophoblast cells are resuspended in a solution of 50-100 microliters PBS/10 mM EDTA. Optionally, the isolated maternal cells are resuspended in a solution of 50-100 microliters PBS/10 mM EDTA. An aliquot of 15 microliters is removed for cell counting and quality control for fetal cells and optionally maternal cells if desired.

Aliquots of 25 microliters of 3× concentrated DNA extraction buffer (90 mM TRIS, 90 mM EDTA, 1.5% EDTA, pH 8.0, 3 mg/ml Proteinase K) are added to 50 microliters of the isolated maternal cells or isolated fetal extravillous trophoblast cells for DNA isolation. These mixtures are then incubated for 3 hrs at 65° C., followed by 10 min at 95° C. The extracted DNA is frozen for PCR assays or can be for further purified by centrifugation at high speed in a microcentrifuge for 5 minutes. Optionally the DNA is still further purified, for example using commercial DNA purification and concentration kits, such as a Zymresearch DNA 10 concentration kit. Pico green of similar reagents can be used for DNA quantification.

Fixed cells were incubated with or without DNase either on beads or in solution. Fixed maternal or fetal cells (500-1500) treated with bead-bound DNase I resulted on average in production of 3-6 ng total DNA.

DNA purification of low amounts of DNA with the Zymresearch DNA concentrator kit led to a 30-50% loss of DNA. On average 2-4 ng pure high-quality DNA is isolated from a single sample of maternal endocervical material retrieved with a cytobrush.

Example 3

RNA Isolation from Fetal Extravillous Trophoblast Cells

A maternal endocervical sample is collected using a cytobrush by inserting it approximately 2 cm into the endocervical canal and rotating 2 or 3 times as it is withdrawn. Mucus present in the canal is also collected in the brush. The cytobrush is rinsed in fixative, for example, a buffered methanol solution. The specimen is stored refrigerated or at ambient temperature and transported to the laboratory for further processing. It can be stored at 4° C. for at least one week without loss of RNA or HLA-G protein.

To isolate RNA from fetal extravillous trophoblast cells, all cells are washed twice with PBS after acidification of the maternal endocervical sample by adding 0.6 ml of acetic acid to the 20-ml volume of buffered methanol solution containing the cells, achieving a final concentration of 3% acetic acid.

The cells are centrifuged through a 250 micron filter, the supernatant is removed and the cell pellet quickly resuspended in 4% paraformaldehyde/PBS for 10 min before again pelleting the cells and washing the cells with PBS or Tris buffer. Formaldehyde fixation prevents loss of highly soluble nucleic acids and effectively inactivates endogenous RNases.

HLA-G-positive fetal extravillous trophoblast cells are removed by immunomagnetic isolation, including the step of incubating of cells with anti-HLA-G antibody affixed to magnetic beads as described in Bolnick et al., Fertil. Steril., 102:135-142.e6, 2014 and maternal cells (HLA-G negative) are separated from magnetized (HLA-G positive) fetal extravillous trophoblast cells using a DynaMag™ Spin magnet (Life Technologies).

The fetal extravillous trophoblast cells are then washed 3 times in PBS with 30 mM of EDTA.

After immunomagnetic isolation of the fetal extravillous trophoblast cells, they are de-cross-linked before RNA isolation by incubation in 200 mM NaCl, 10 mM Tris-HCl pH 8.0, 1 mM EDTA and 1% SDS and 1300 µg/ml Proteinase K at 56° C. for 15 min and 80° C. for 15 min. The lysate is then treated with 180 Kunitz units DNase/milliliter to remove DNA after washing. The RNA in the lysate is then purified using a spin column and eluted with RNAse-free water. The isolated RNA is quantified and assessed for purity with an Agilent 2100 Electrophoresis Microfluidics Analyzer, using the RNA Pico Kit (Agilent Technologies).

Optional DNase treatment prior to cell lysis eliminated DNA contamination before extraction of RNA, which was fragmented during de-crosslinking.

Figure 2:
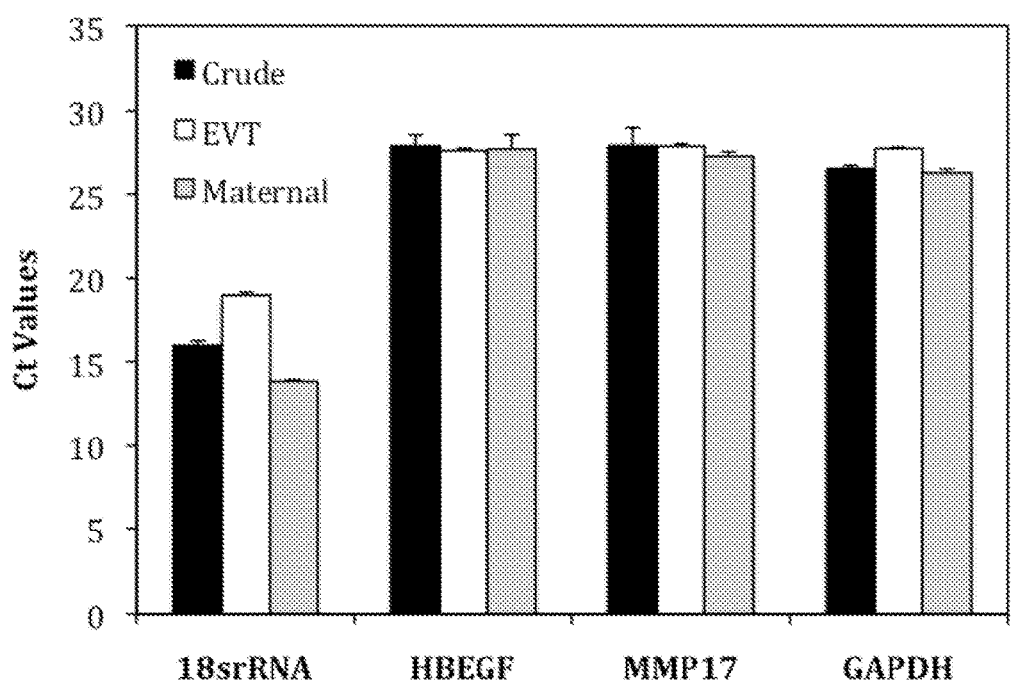
FIG. 2 is a graph showing Ct values from quantitative PCR (qPCR) of four RNAs of different known abundance from crude ThinPrep specimens, isolated fetal extravillous trophoblast cells (EVT) and fetal extravillous trophoblast cell-depleted maternal cells (maternal)

Isolated RNA was quantified and its purity assessed using an Agilent 2100 Electrophoresis Microfluidics Analyzer with the RNA Pico Kit (Agilent Technologies). The quality of the fragmented RNA was validated by semi-quantitative real-time PCR using a CFX384 BioRad thermal cycler (Life Technologies). RNA recoveries from 19 maternal endocervical specimens were evaluated as shown in FIG. 1 and Ct values from qPCR of four RNAs of different known abundance are shown in FIG. 2 for the crude ThinPrep specimen, isolated fetal extravillous trophoblast cells and fetal extravillous trophoblast cell-depleted maternal cells. For FIG. 2, cDNA made from equal amounts of RNA was assayed by qPCR with primers for the indicated rRNA or mRNAs. The quantities of RNA recovered in the fetal extravillous trophoblast cells and maternal isolates were comparable to the crude unfractionated cervical specimen. RNA from isolated fetal extravillous trophoblast cells (EVT) was compared to RNA isolated from the maternal sample, which did not require aldehyde fixation since cells were used directly without EVT isolation. Although analysis showed the RNA in isolates to be highly fragmented, it produced Ct values comparable to the crude cells when equivalent amounts of RNA were assayed by qPCR for four different RNAs. It was found that about 50 ng of useful RNA was recovered using this approach. RNA isolation from isolated fetal extravillous trophoblast cells according to the present invention generated adequate amounts of RNA from fetal extravillous trophoblast cells for analysis by qPCR.

Figure 3:
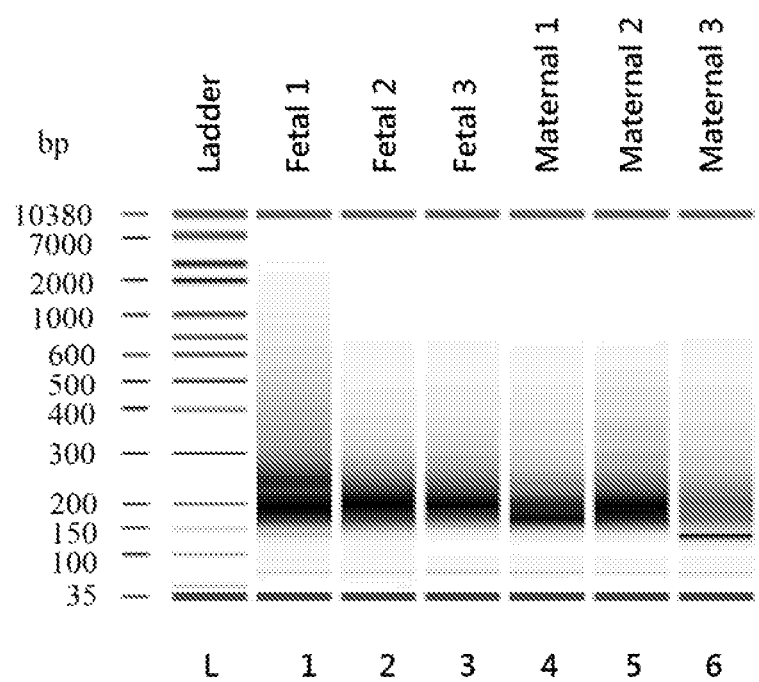
FIG. 3 is an image of a gel showing results of electrophoresis of RNA isolated from 3 fetal and 3 maternal preparations from a single maternal endocervical specimen.
Figure 4A:
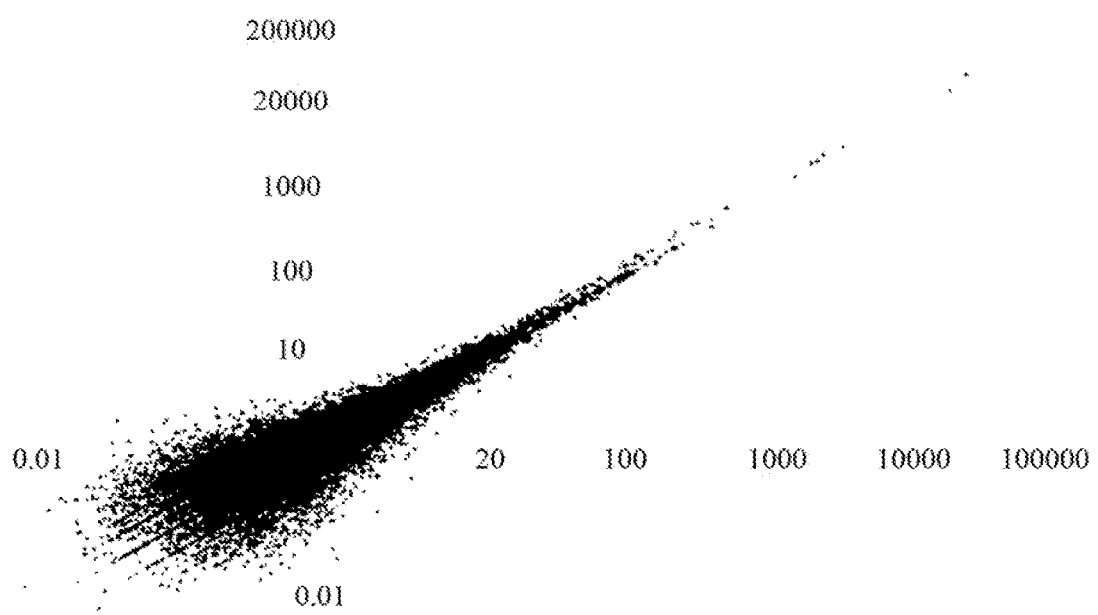
FIG. 4A is a plot showing results of RNA sequencing and comparison of RNA expression levels in two maternal samples as "reads per kilobase of transcript per million mapped reads" (RPKM) values demonstrating the similarity of the two maternal RNA samples.
Figure 4B:
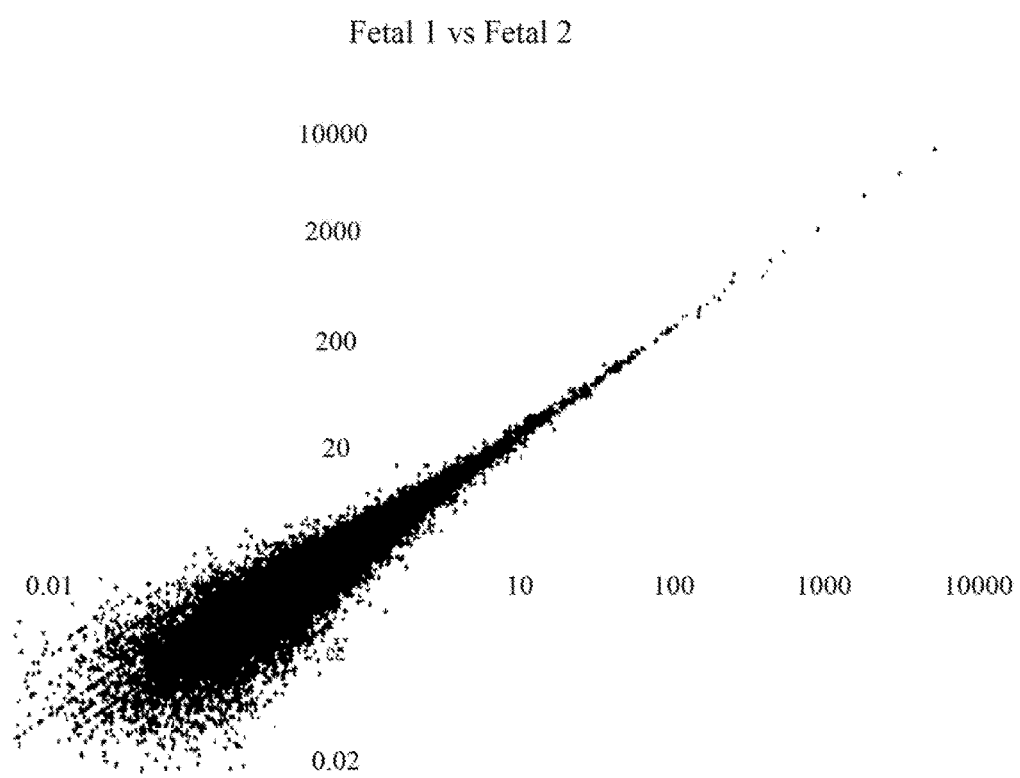
FIG. 4B is a plot showing results of RNA sequencing and comparison of RNA expression levels in two fetal samples as RPKM values demonstrating the similarity of the two fetal RNA samples.

The isolated RNA was then used to construct libraries for RNA sequencing by generating barcoded libraries using the ScriptSeq v2 RNA-Seq Library Preparation Kit (Epicentre) (FIG. 3). RNA isolated from fetal and maternal cells in a single specimen were sequenced in triplicate on an Illumina Genome Analyzer II sequencer. After sequencing, the RNA data was subjected to demultiplexing software. The sequencing data was aligned to the human genome build (HG19) and to the ribosomal sequences, 18s and 28s, using bioinformatics tool Novoalign. A 95% alignment was obtained, suggesting the success of both the RNA library preparation and demultiplexing. Over 20,000 gene products were identified in each specimen. The reads thus generated were converted into bed.files and imported to the Genomatix mapping station (GMS). The GMS generated data in the form of RPKM (Reads Per Kilobase of exon per Million fragments mapped) for the 25,000 genes in the database. Comparison of the RPKM values among the samples showed close alignment between maternal samples or fetal samples, but clear outliers when fetal and maternal samples were aligned. Examples of each comparison are shown in FIGS. 4A-4C. Using RNA obtained by crosslinking EVT cells with paraformaldehyde during their isolation, high quality data through next generation sequencing analysis was generated.

Example 4

Figure 5A:
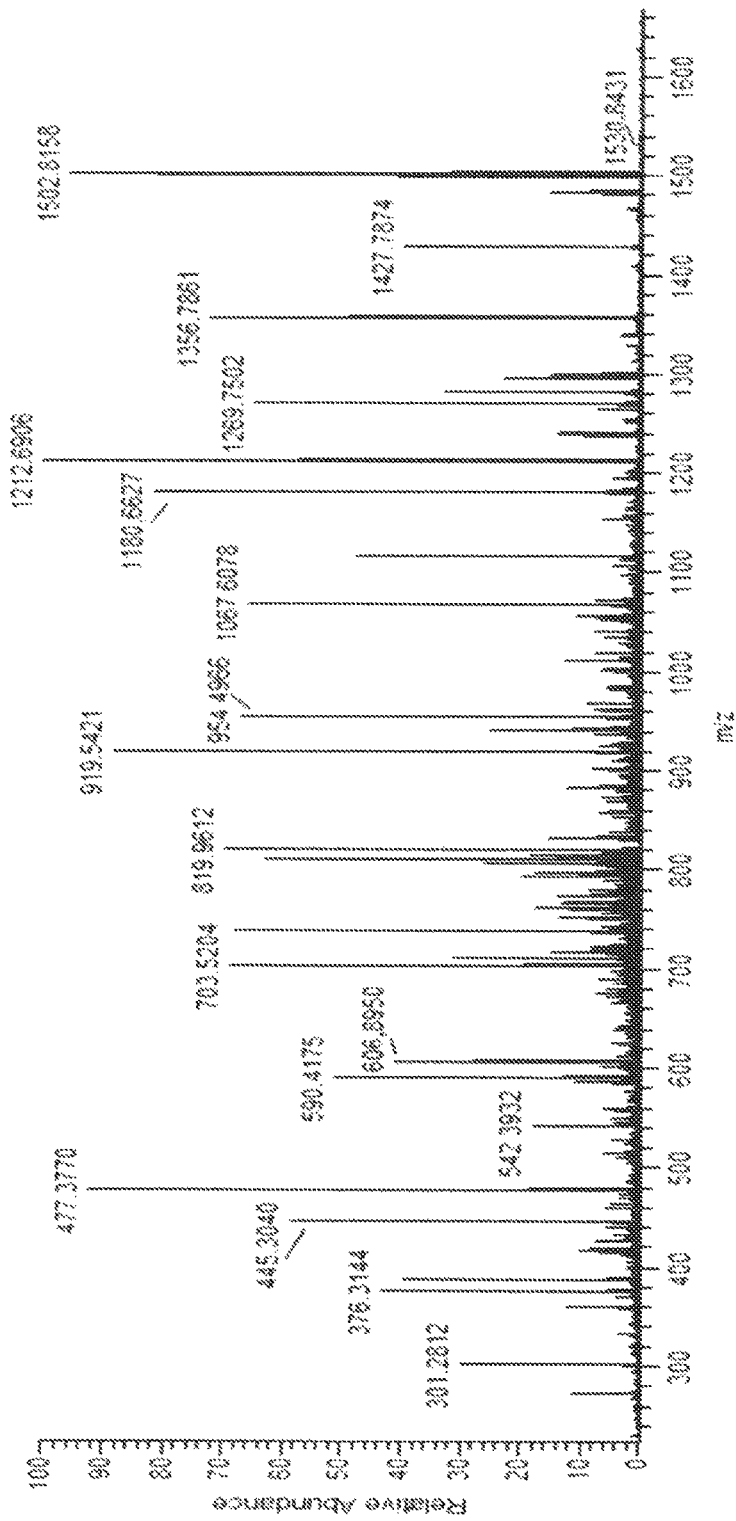
FIG. 5A is a graph showing MS2 sequencing spectrum for the m/z 829.01 ion in Synchronized Precursor Selection (SPS) analysis of TMT10plex-labeled HRT-8/SVneo cells.
Figure 5B:
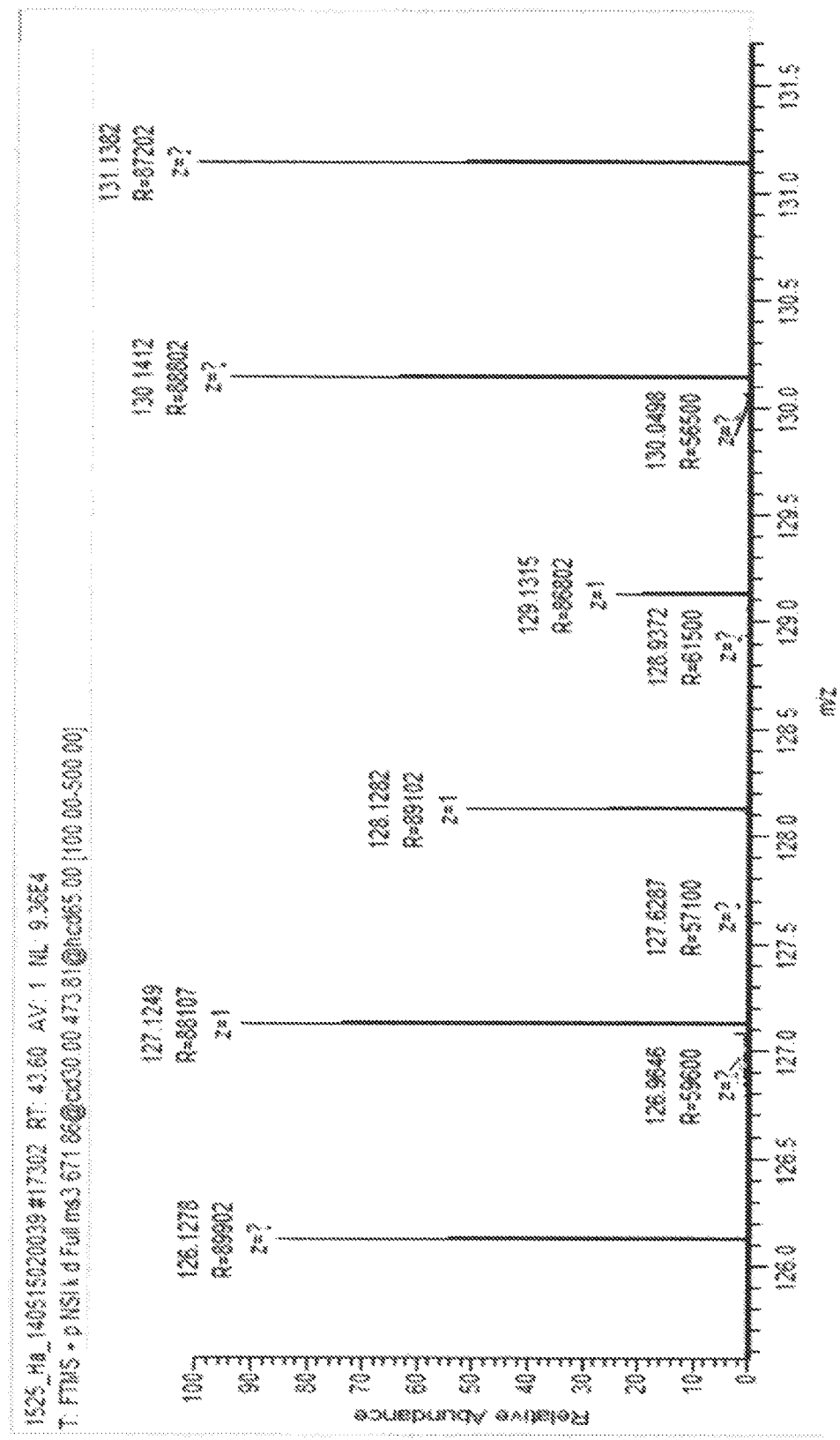
FIG. 5B is a graph showing MS2 sequencing spectrum for reporter ions 126 through 131 at medium resolution in Synchronized Precursor Selection (SPS) analysis of TMT10plex-labeled HRT-8/SVneo cells.
Figure 5C:
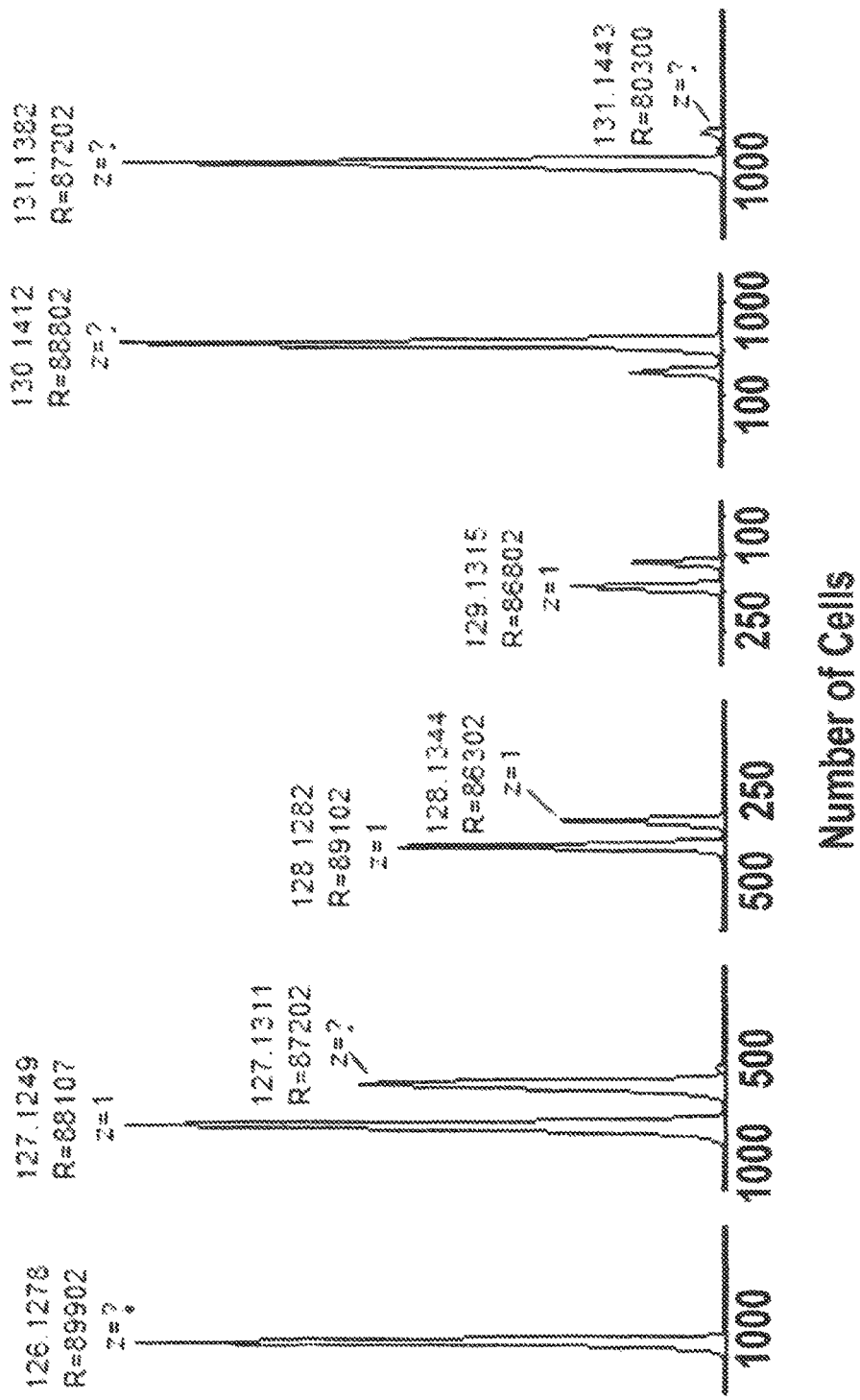
FIG. 5C is a graph showing MS2 sequencing spectrum for reporter ions 126 through 131 at high resolution in Synchronized Precursor Selection (SPS) analysis of TMT10plex-labeled HRT-8/SVneo cells in which channels from m/z 126 to m/z 131 contained the indicated number of HRT cells.

For deep proteome profiling in rare cell populations, a multiplexed analysis according to aspects of the present invention incorporates a reference sample from the closely related HTR-8/SVneo (HTR) cytotrophoblast cell line. Each channel in the sample contains 100 to 1000 cells. The signal for selection of ions in the MS1 and sequencing of those ions in the MS2 are additive, providing amplification of the signals for peptides in the 100-cell samples in combination with the other multiplexed samples. Synchronized Precursor Selection (SPS), in which 10 MS2 ions are combined to generate an MS3 spectrum for quantification, is used to increase specificity and sensitivity as described in Ting et al., Nat Methods 2011; 8: 937-940; and McAlister et al., Anal Chem 2012; 84: 7469-7478. The assignment and relative quantification of the proteins for individual samples occurs in the MS3 spectra, as illustrated in FIGS. 5A-5C, which shows an MS2 spectrum (FIG. 5A) and the corresponding quantification MS3 spectrum (FIGS. 5B-5C). Here, trophoblast cells were aliquoted at 1000, 500, 250 or 100 cells per tube. The cells were lysed with ProteaseMax detergent, a mass spec friendly detergent that does not need to be removed from the sample. Lysed cells were digested with Trypsin/Lys-C after being reduced and alkylated with minimal concentrations of TCEP and iodoacetamide (IAA). Following an overnight digestion, the peptides were labeled with sufficient TMT10plex reagent (Thermo Scientific) for 5 micrograms of protein. The labeled peptides were pooled, concentrated by Speed-Vac and run directly on the Orbitrap Fusion using SPS to acquire quantification spectra. Quantification of smaller cell samples was determined by the ratio of signal compared to the '126' channel that contained 1000 cells. These ratios were: 0.99, 1.031 and 1.031 for the three other 1000 cell samples; 0.523 and 0.559 for the 500 cell samples; 0.226 and 0.232 for the 250 cell samples and 0.124 and 0.141 for the 100 cell samples (FIG. 5C). In a 90-min gradient from 2 to 30% acetonitrile 931 proteins that represented a broad range of cellular organelles and biochemical activities were identified and quantified. All proteins that were identified were quantified in all 10 channels indicating that the 100 cell samples were profiled to the same depth as the 1000 cell samples. Note there was prominent representation by 109 proteins in the Reproduction and Reproductive Process categories, as would be expected for trophoblast cells. These data represent an important breakthrough in quantitative proteome profiling of rare cell populations. The same procedures are used in analysis of fetal extravillous trophoblast cells to identify differences between patient cohorts.

Example 5

Biomarkers for Preeclampsia (PE) and Intrauterine Growth Restriction (IUGR).

Isolation of Cells According to Example

Figure 6:
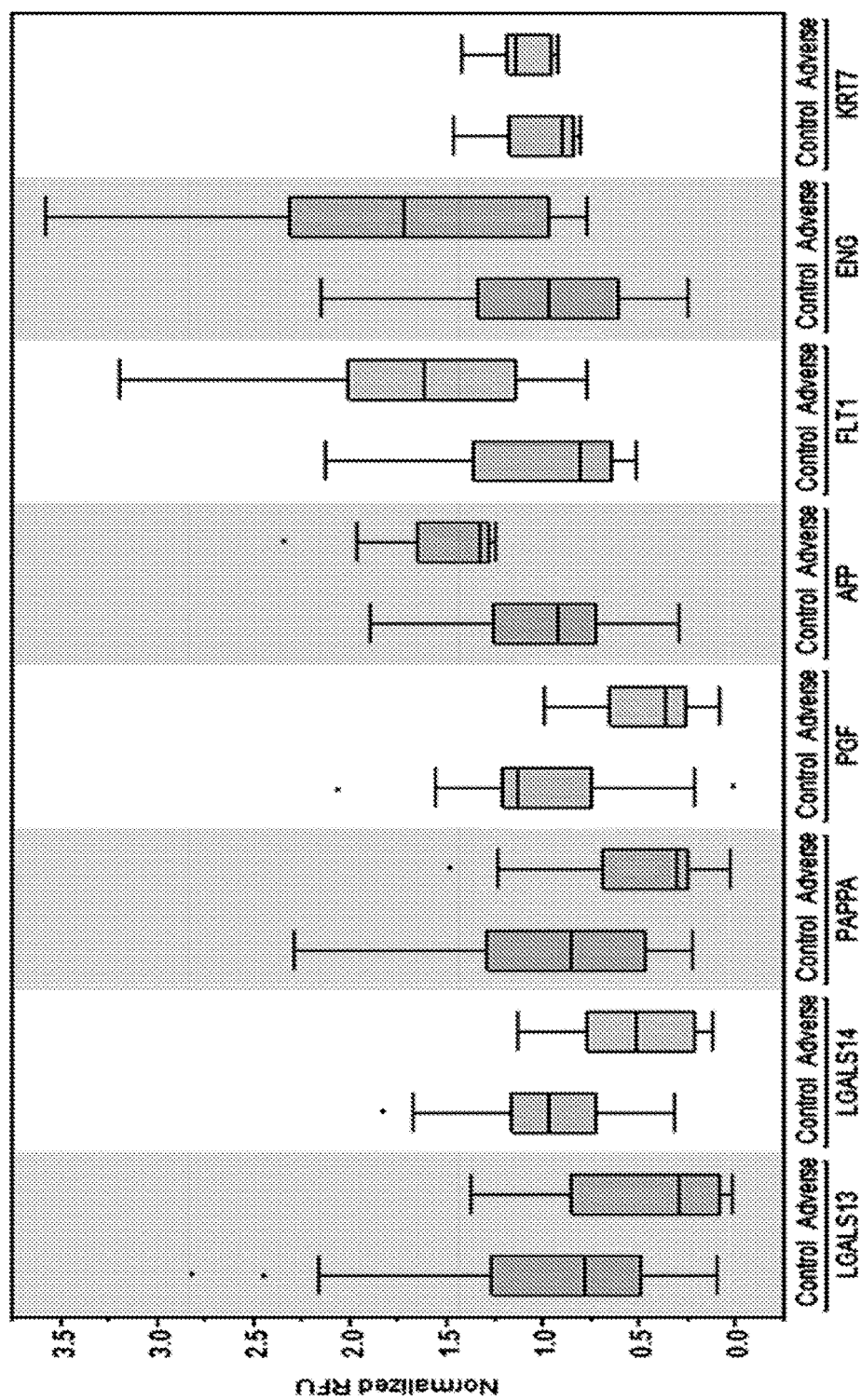
FIG. 6 is a graph showing expression of biomarkers in fetal extravillous trophoblast cells obtained by a method according to aspects of the present invention; median fluorescence intensities (RFU) are shown n box plots where the horizontal line is the median, the box delineates the first quartiles away from the median, the bars indicate the second quartiles away from the median and outliers are indicated as dots. Each pair of control and adverse pregnancies was significantly different, according to the Wilcoxon signed-rank test, except KRT7.
Figure 7:
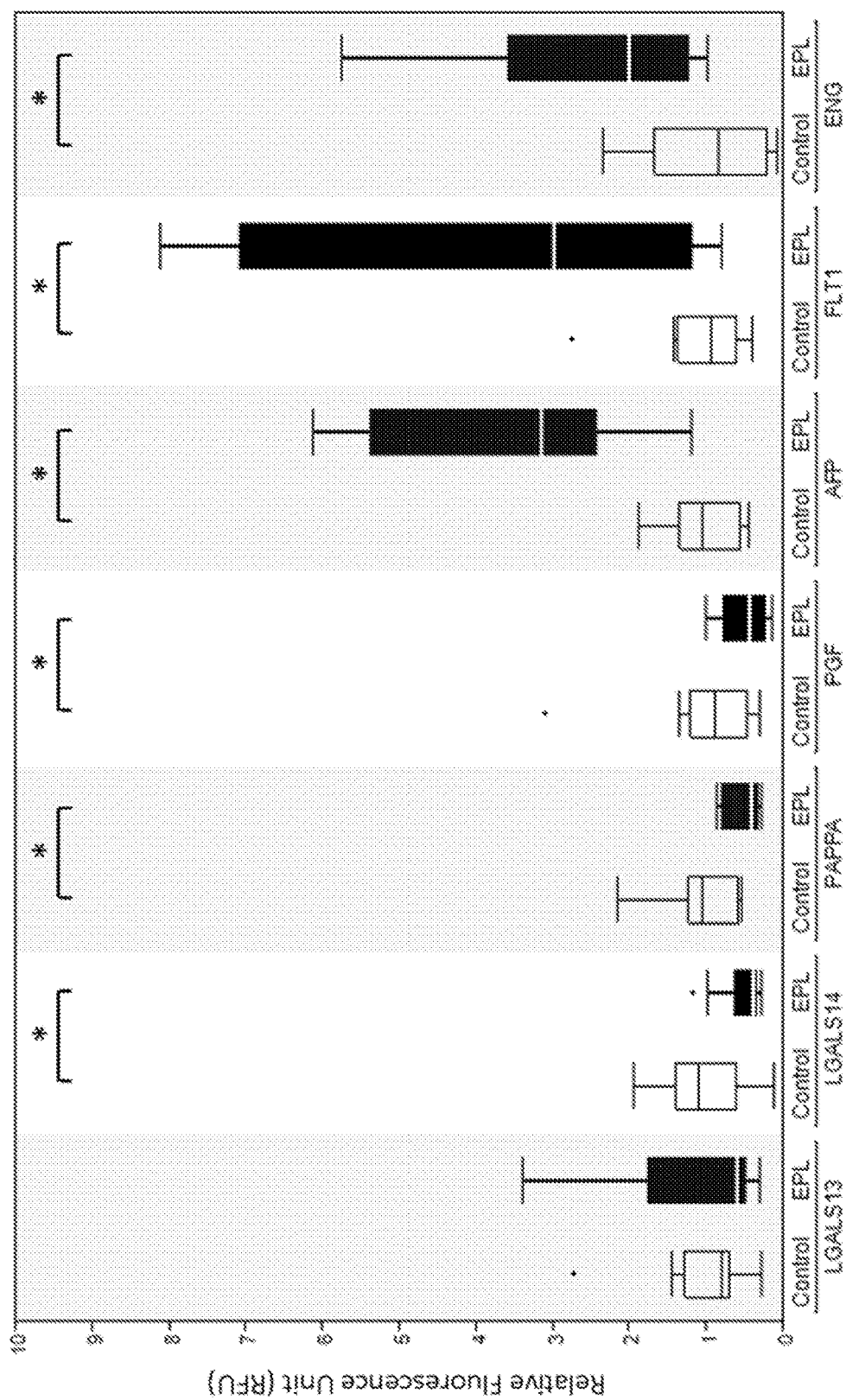
FIG. 7 is a graph showing quantification of biomarker expression in trophoblast retrieval and isolation from the cervix (TRIC)-isolated extravillous trophoblast (EVT) cells; the EVT cells labeled with antibodies against the indicated proteins were imaged to obtain the relative fluorescence unit (RFU) values, as described in the Examples; the nonparametric Wilcoxon test was employed to compare the expression of each protein marker between control (white) and early pregnancy loss (EPL) (black) groups; the significant differences ($P<0.05$) are indicated by a bar and asterisk above the control/EPL pairs. Box=25th to 75th percentiles; horizontal line within the box=median; whisker=1.5×Interquartile range (3rd quartile to 1st quartile); the dots represent individual outliers.

Screening fetal extravillous trophoblast cells obtained from first and second trimester pregnancies by semi-quantitative immunocytochemistry revealed that seven proteins associated with preeclampsia and intrauterine growth restriction galectin 13 (LGALS13, a.k.a. PP13), galectin 14 (LGALS14), placental growth factor (PGF), pregnancy-associated plasma protein A (PAPPA), alpha fetal protein (AFP), endoglin (ENG), or fms-related tyrosine kinase 1 (FLT-1) are significantly altered. Specifically, three proteins significantly increase (AFP, FLT1, ENG) and four proteins decrease (PAPPA, PGF, LGALS13, LGALS14) in pregnancies that later developed preeclampsia or intrauterine growth restriction, while keratin-7 (KRT7) levels were similar in both groups (FIG. 6). Medical records were reviewed to select archived specimens for analysis from pregnancies with either a normal outcome (N=20) or development of uteroplacental insufficiency (preeclampsia or intrauterine growth restriction; N=12). Specimens were obtained by TRIC at similar (p=034) gestational age (GA), ranging from 5 to 20 weeks (average GA=10.9 weeks for normal; 12.7 weeks for PE/IUGR). Immunofluorescence intensities of individual cells were semi-quantified using immunocytochemistry and image analysis (Simple PCI, Hamamatsu), as described in Wang et al., Dev Biol 2007; 302: 143-153; and Rout et al., Dev Biol 2004; 268: 135-151. Antibodies were each titered to ensure a linear fluorescence signal with labeling. Slides were assessed together with the same lots of antibodies, using similar camera exposure times to optimize signal quantification. Averages of 10 cells were determined, subtracting background staining produced by non-immune IgG. KRT7, which did not change (FIG. 6), provided a control for non-specific variances. Significant differences (t-tests, adjusted for equal or unequal variances) in expression were found between the normal and PE/IUGR cohorts for each of the putative biomarker proteins (FIG. 6). There was no correlation between stain intensity and GA within the normal cohort, although power was probably inadequate. Receiver operating characteristic (ROC) curves constructed for each protein had areas under the curves (AUCs) as shown in Table I below.

TABLE I

| Biomarker | AUC | Cut-off | Tendency in Adverse |
|---|---|---|---|
| LGALS13 | 0.75 | 17.54 | Lower value |
| LGALS14 | 0.80 | 27.4 | Lower value |

TABLE I-continued

| Biomarker | AUC | Cut-off | Tendency in Adverse |
|---|---|---|---|
| PAPPA | 0.78 | 15.47 | Lower value |
| PGF | 0.82 | 18.73 | Lower value |
| AFP | 0.88 | 17.45 | Higher value |
| FLT1 | 0.78 | 21.12 | Higher value |
| ENG | 0.77 | 14.02 | Higher value |

Example 6

Biomarkers for Spontaneous Abortion and Preterm Birth.

Fetal extravillous trophoblast cells collected in the first and second trimester from 8 patients with known spontaneous abortions and 13 patients with uncomplicated term pregnancies were analyzed by quantitative immunocytochemistry, using a panel of 7 proteins AFP, FLT1, ENG, PAPPA, PGF, LGALS13 and LGALS14. Average gestational age was 7.2 weeks in the spontaneous abortion patients and 10.9 in the control patients. Significant elevations in ENG, Flt-1, and AFP and a significant decrease in LGALS14 were seen in spontaneous abortion patients vs. control patients (Table II). Abnormal protein expression is apparent early in pregnancy in fetal extravillous trophoblast cells in spontaneous abortion patients.

Table II details the expression of protein biomarkers in patients with normal pregnancy outcomes (Control) and patients that had a spontaneous abortion. Average fluorescence intensities±SEM are shown and P values derived from t-tests conducted for each protein to compare control and spontaneous abortion patient groups.

TABLE II

| | ENG | FLT-1 | AFP | LGALS14 |
|---|---|---|---|---|
| Control | 20.44 ± 5.61 | 18.50 ± 4.05 | 11.68 ± 1.93 | 54.77 ± 6.71 |
| Spontaneous Abortion | 70.71 ± 14.60 | 79.27 ± 15.01 | 52.23 ± 5.94 | 38.19 ± 5.33 |
| P Value | 0.009 | 0.001 | <0.001 | 0.02 |

Items

1. A method of assaying RNA from fetal extravillous trophoblast cells, comprising:

obtaining a maternal endocervical sample from a pregnant subject;

removing fetal extravillous trophoblast cells from the maternal endocervical sample, producing isolated fetal extravillous trophoblast cells;

fixing fetal extravillous trophoblast cells by treatment with an aldehyde fixative producing aldehyde fixed fetal extravillous trophoblast cells;

washing the aldehyde fixed fetal extravillous trophoblast cells or washing a lysate of the isolated aldehyde fixed fetal extravillous trophoblast cells to promote removal of the crosslinks introduced by the aldehyde fixative, producing washed fetal extravillous trophoblast cells or a washed lysate;

extracting fetal extravillous trophoblast cell RNA from the washed fetal extravillous trophoblast cells or washed lysate; and assaying the fetal extravillous trophoblast cell RNA to determine one or more characteristics of the fetal extravillous trophoblast cell RNA.

2. The method of item 1, wherein the treatment with the aldehyde fixative is performed prior to and/or following removing fetal extravillous trophoblast cells from the maternal endocervical sample.

3. The method of item 1, wherein the maternal endocervical sample is fixed immediately after obtaining the sample from the pregnant subject.

4. The method of any of items 1-3, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells.

5. The method of any of items 1-3, wherein the maternal endocervical sample is fixed by treatment with the aldehyde fixative immediately after obtaining the sample from the pregnant subject.

6. The method of any of items 1-5, wherein assaying the fetal extravillous trophoblast cell RNA comprises sequencing, PCR, quantitative PCR, real-time PCR or a combination of any two or more thereof.

7. The method of any of items 1-6, wherein the pregnant subject is human.

8. The method of any of items 1-7, wherein removing fetal extravillous trophoblast cells from the maternal endocervical sample comprises contacting the fetal extravillous trophoblast cells with an antibody specific for the fetal extravillous trophoblast cells, wherein the antibody does not bind to maternal cells in the maternal endocervical sample.

9. The method of any of items 1-8, wherein the antibody specific for the fetal extravillous trophoblast cells is attached to a support.

10. The method of any of items 1-9, wherein no Protein A or Protein G is attached to the support.

11. The method of any of items 1-10, wherein the support is a plurality of magnetic particles.

12. The method of any of items 1-11, wherein removing fetal extravillous trophoblast cells from the maternal endocervical sample comprises exposure of the magnetic particles to a magnet.

13. The method of any of items 1-12, wherein the maternal endocervical sample is not treated with a mucolytic agent.

14. A method of assaying fetal extravillous trophoblast cells, comprising:
obtaining a maternal endocervical sample from a pregnant subject;
contacting the maternal endocervical sample with a first antibody, the first antibody specific for the fetal extravillous trophoblast cells, wherein the first antibody does not bind to maternal cells in the maternal endocervical sample;
contacting the maternal endocervical sample with one more additional antibodies, wherein the first antibody and each additional antibody is distinguishably labeled with different labels detectable by inductively coupled plasma mass spectrometry;
nebulizing the maternal endocervical sample to separate cells; and
performing inductively coupled plasma mass spectrometry on the cells, thereby assaying the fetal extravillous trophoblast cells.

15. The method of item 14, wherein the first antibody is specific for major histocompatibility complex, class I, G (HLA-G).

16. The method of item 14 or 15, wherein the one or more additional antibodies is an antibody specific for a protein selected from the group consisting of: galectin 13, galectin 14, placental growth factor, pregnancy-associated plasma protein A, alpha fetal protein, endoglin, fms-related tyrosine kinase 1 and keratin-7.

17. The method of any of items 14-16, wherein the maternal endocervical sample is not treated with a mucolytic agent.

18. The method of any of items 1-17 wherein the maternal endocervical sample from a pregnant subject is collected at about three weeks after conception (gestational age 5 weeks) or later during the pregnancy.

18. A method of assaying isolated fetal extravillous trophoblast cells substantially as described herein.

19. A method of assaying isolated fetal extravillous trophoblast cell RNA substantially as described herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of assaying RNA from fetal extravillous trophoblast cells, comprising:
obtaining a maternal endocervical sample from a pregnant subject;
removing fetal extravillous trophoblast cells from the maternal endocervical sample, producing isolated fetal extravillous trophoblast cells;
fixing fetal extravillous trophoblast cells by treatment with an aldehyde fixative producing aldehyde fixed fetal extravillous trophoblast cells;
washing the aldehyde fixed fetal extravillous trophoblast cells or washing a lysate of the isolated aldehyde fixed fetal extravillous trophoblast cells to promote removal of the crosslinks introduced by the aldehyde fixative, producing washed fetal extravillous trophoblast cells or washed lysate;
extracting fetal extravillous trophoblast cell RNA from the washed fetal extravillous trophoblast cells or washed lysate, thereby isolating the fetal extravillous trophoblast cell RNA from DNA; and
assaying the fetal extravillous trophoblast cell RNA to determine one or more characteristics of the fetal extravillous trophoblast cell RNA.

2. The method of claim 1, wherein the treatment with the aldehyde fixative is performed prior to and/or following removing fetal extravillous trophoblast cells from the maternal endocervical sample.

3. The method of claim 1, wherein the maternal endocervical sample is fixed immediately after obtaining the sample from the pregnant subject.

4. The method of any of claim 1, wherein the maternal endocervical sample is fixed in an alcohol fixative immediately after obtaining the sample from the pregnant subject and prior to fixing fetal extravillous trophoblast cells by treatment with the aldehyde fixative producing aldehyde fixed fetal extravillous trophoblast cells.

5. The method of any of claim 1, wherein the maternal endocervical sample is fixed by treatment with the aldehyde fixative immediately after obtaining the sample from the pregnant subject.

6. The method of any of claim 1, wherein assaying the fetal extravillous trophoblast cell RNA comprises sequencing, PCR, quantitative PCR, real-time PCR or a combination of any two or more thereof.

7. The method of claim 1, wherein the pregnant subject is human.

8. The method of claim 1, wherein removing fetal extravillous trophoblast cells from the maternal endocervical sample comprises contacting the fetal extravillous trophoblast cells with an antibody specific for the fetal extravillous trophoblast cells, wherein the antibody does not bind to maternal cells in the maternal endocervical sample.

9. The method of claim 8, wherein the antibody specific for the fetal extravillous trophoblast cells is attached to a support.

10. The method of claim 9, wherein no Protein A or Protein G is attached to the support.

11. The method of claim 9, wherein the support is a plurality of magnetic particles.

12. The method of claim 11, wherein removing fetal extravillous trophoblast cells from the maternal endocervical sample comprises exposure of the magnetic particles to a magnet.

13. The method of claim 1, wherein the maternal endocervical sample is not treated with a mucolytic agent.

* * * * *

UNITED STATES PATENT AND TRADEMARK OFFICE
CERTIFICATE OF CORRECTION

PATENT NO. : 10,330,680 B2
APPLICATION NO. : 15/517882
DATED : June 25, 2019
INVENTOR(S) : D. Randall Armant et al.

Page 1 of 1

It is certified that error appears in the above-identified patent and that said Letters Patent is hereby corrected as shown below:

In the Specification

Column 1, Line 13, insert:
--GOVERNMENT SUPPORT
This invention was made with government support under Grant No. R21 HD071408 awarded by the National Institutes of Health. The Government has certain rights in the invention.--.

In the Claims

Column 32, Line 58 Claim 4: After "method" delete "of any";

Column 32, Line 64 Claim 5: After "method" delete "of any"; and

Column 33, Line 1 Claim 6: After "method" delete "of any".

Signed and Sealed this
Sixth Day of August, 2019

Andrei Iancu
*Director of the United States Patent and Trademark Office*